US010414737B2

(12) United States Patent
Bremner et al.

(10) Patent No.: US 10,414,737 B2
(45) Date of Patent: Sep. 17, 2019

(54) PROCESS METHODS FOR PHOSPHATIDYLINOSITOL 3-KINASE INHIBITORS

(71) Applicant: GILEAD CALISTOGA LLC, Foster City, CA (US)

(72) Inventors: Stacy Bremner, Edmonton (CA); Jerry B. Evarts, Seattle, WA (US); Keiko Sujino, Edmonton (CA); Duong Tran, Edmonton (CA); Dragos Vizitiu, Edmonton (CA)

(73) Assignee: Gilead Sciences, Inc., Foster City, CA (US)

( * ) Notice: Subject to any disclaimer, the term of this patent is extended or adjusted under 35 U.S.C. 154(b) by 0 days.

(21) Appl. No.: 16/025,862

(22) Filed: Jul. 2, 2018

(65) Prior Publication Data
US 2019/0031626 A1    Jan. 31, 2019

Related U.S. Application Data

(60) Continuation of application No. 15/817,044, filed on Nov. 17, 2017, now Pat. No. 10,047,060, which is a division of application No. 15/392,198, filed on Dec. 28, 2016, now Pat. No. 10,059,677, which is a division of application No. 14/575,670, filed on Dec. 18, 2014, now Pat. No. 9,567,337.

(60) Provisional application No. 61/919,548, filed on Dec. 20, 2013.

(51) Int. Cl.
C07D 265/22 (2006.01)
C07D 239/91 (2006.01)
C07C 233/90 (2006.01)
C07D 263/58 (2006.01)
C07D 473/34 (2006.01)
C07C 265/10 (2006.01)
C07D 487/04 (2006.01)

(52) U.S. Cl.
CPC .......... *C07D 265/22* (2013.01); *C07C 233/90* (2013.01); *C07C 265/10* (2013.01); *C07D 239/91* (2013.01); *C07D 263/58* (2013.01); *C07D 473/34* (2013.01); *C07D 487/04* (2013.01)

(58) Field of Classification Search
CPC .... C07D 473/34; C07D 265/22; C07C 233/90
USPC .......................................................... 544/92
See application file for complete search history.

(56) References Cited

U.S. PATENT DOCUMENTS

| 3,322,756 A | 5/1967 | Ruschig et al. |
| 3,691,016 A | 9/1972 | Patel |
| 3,897,432 A | 7/1975 | Shen et al. |
| 3,969,287 A | 7/1976 | Jaworek et al. |
| 3,984,555 A | 10/1976 | Amschler et al. |
| 4,179,337 A | 12/1979 | Davis et al. |
| 4,183,931 A | 1/1980 | Wolfe et al. |
| 4,195,128 A | 3/1980 | Hidebrand et al. |
| 4,225,489 A | 9/1980 | Rolf et al. |
| 4,229,537 A | 10/1980 | Hodgins et al. |
| 4,247,642 A | 1/1981 | Hirohara et al. |
| 4,289,872 A | 9/1981 | Denkewalter et al. |
| 4,301,144 A | 11/1981 | Iwashita et al. |
| 4,330,440 A | 5/1982 | Ayers et al. |
| 4,496,689 A | 1/1985 | Mitra |
| 4,640,835 A | 2/1987 | Shimizu et al. |
| 4,670,417 A | 6/1987 | Iwasaki et al. |
| 4,791,192 A | 12/1988 | Nakagawa et al. |
| 4,925,673 A | 5/1990 | Steiner et al. |
| 4,943,593 A | 7/1990 | Palfreyman et al. |
| 4,965,288 A | 10/1990 | Palfreyman et al. |
| 4,997,854 A | 3/1991 | Kagan et al. |
| 5,013,556 A | 5/1991 | Woodle et al. |
| 5,021,456 A | 6/1991 | Palfreyman et al. |
| 5,059,714 A | 10/1991 | Palfreyman et al. |
| 5,120,764 A | 6/1992 | McCarthy et al. |
| 5,182,297 A | 1/1993 | Palfreyman et al. |
| 5,225,347 A | 7/1993 | Goldberg et al. |
| 5,229,490 A | 7/1993 | Tam |
| 5,252,608 A | 10/1993 | Palfreyman et al. |
| 5,378,725 A | 1/1995 | Bonjouklian et al. |
| 5,480,906 A | 1/1996 | Creemer et al. |
| RE35,862 E | 7/1998 | Steiner et al. |
| 5,858,753 A | 1/1999 | Chantry et al. |
| 5,882,910 A | 3/1999 | Chantry et al. |
| 5,948,664 A | 9/1999 | Williams et al. |
| 5,985,589 A | 11/1999 | Chantry et al. |
| 6,046,049 A | 4/2000 | Monia et al. |
| 6,048,970 A | 4/2000 | Lal et al. |
| 6,277,981 B1 | 8/2001 | Tu et al. |
| 6,291,220 B1 | 9/2001 | Williams et al. |
| 6,369,038 B1 | 4/2002 | Blumenfeld et al. |

(Continued)

FOREIGN PATENT DOCUMENTS

CN    101031569 A    9/2007
EP    0 525 960 A1   2/1993

(Continued)

OTHER PUBLICATIONS

"Acute Congestive Heart Failure", Thomas N. Levin, Postgraduate Medicine, vol. 101, No. 1, 1997.

(Continued)

*Primary Examiner* — Kahsay Habte
(74) *Attorney, Agent, or Firm* — Morrison & Foerster LLP

(57) ABSTRACT

A process for the synthesis of quinazolinone containing compounds which may be useful for the treatment of cancer, is hereby disclosed. In addition, compound intermediates relating to these processes are also disclosed.

24 Claims, No Drawings

(56) References Cited

U.S. PATENT DOCUMENTS

| | | |
|---|---|---|
| 6,410,224 B1 | 6/2002 | Stinchcomb et al. |
| 6,426,337 B1 | 7/2002 | Cox et al. |
| 6,482,623 B1 | 11/2002 | Vanhaesebroeck et al. |
| 6,518,277 B1 | 2/2003 | Sadhu et al. |
| 6,667,300 B2 | 12/2003 | Sadhu et al. |
| 6,696,250 B1 | 2/2004 | Cech et al. |
| 6,800,620 B2 | 10/2004 | Sadhu et al. |
| 6,949,535 B2 | 9/2005 | Sadhu et al. |
| 7,161,002 B2 | 1/2007 | Bergnes et al. |
| 7,932,260 B2 | 4/2011 | Fowler et al. |
| 8,138,195 B2 | 3/2012 | Sadhu et al. |
| 8,207,153 B2 | 6/2012 | Fowler et al. |
| 8,492,389 B2 | 7/2013 | Sadhu et al. |
| RE44,599 E | 11/2013 | Fowler et al. |
| 8,586,597 B2 | 11/2013 | Fowler et al. |
| RE44,638 E | 12/2013 | Fowler et al. |
| 8,623,881 B2 | 1/2014 | Sadhu et al. |
| 8,637,533 B2 | 1/2014 | Sadhu et al. |
| 8,653,077 B2 | 2/2014 | Sadhu et al. |
| 8,779,131 B2 | 7/2014 | Kesicki et al. |
| 8,865,730 B2 | 10/2014 | Carra et al. |
| 8,980,901 B2 | 3/2015 | Fowler et al. |
| 8,993,583 B2 | 3/2015 | Fowler et al. |
| 9,149,477 B2 | 10/2015 | Kesicki et al. |
| 9,487,772 B2 | 11/2016 | Sadhu et al. |
| 9,567,337 B2 | 2/2017 | Bremner et al. |
| 9,708,327 B2 | 7/2017 | Buttar et al. |
| 10,010,550 B2 | 7/2018 | Sadhu et al. |
| 10,047,060 B2 | 8/2018 | Bremner et al. |
| 10,059,677 B2 | 8/2018 | Bremner et al. |
| 2004/0023390 A1 | 2/2004 | Davidson et al. |
| 2004/0092561 A1 | 5/2004 | Ruckle et al. |
| 2004/0121996 A1 | 6/2004 | Barvian et al. |
| 2004/0138199 A1 | 7/2004 | Goglietti et al. |
| 2004/0242631 A1 | 12/2004 | Garlich et al. |
| 2004/0248871 A1 | 12/2004 | Farjanel et al. |
| 2004/0248953 A1 | 12/2004 | Gogliotti et al. |
| 2004/0248954 A1 | 12/2004 | Gogliotti et al. |
| 2004/0259926 A1 | 12/2004 | Bruendle et al. |
| 2005/0004195 A1 | 1/2005 | Para et al. |
| 2005/0020630 A1 | 1/2005 | Connolly et al. |
| 2005/0020631 A1 | 1/2005 | Gogliotti et al. |
| 2005/0043239 A1 | 2/2005 | Douangpanya et al. |
| 2005/0054614 A1 | 3/2005 | Diacovo et al. |
| 2005/0239809 A1 | 10/2005 | Watts et al. |
| 2006/0079538 A1 | 4/2006 | Hallahan et al. |
| 2006/0106038 A1 | 5/2006 | Bouscary et al. |
| 2008/0287469 A1 | 11/2008 | Diacovo et al. |
| 2010/0029693 A1 | 2/2010 | Douangpanya et al. |
| 2010/0202963 A1 | 8/2010 | Gallatin et al. |
| 2010/0249155 A1 | 9/2010 | Evarts et al. |
| 2010/0256167 A1 | 10/2010 | Fowler et al. |
| 2011/0044942 A1 | 2/2011 | Puri et al. |
| 2011/0230465 A1 | 9/2011 | Stammers et al. |
| 2012/0015964 A1 | 1/2012 | Fowler et al. |
| 2012/0040980 A1 | 2/2012 | Huggins et al. |
| 2013/0252976 A1 | 9/2013 | Carra |
| 2014/0154772 A1 | 6/2014 | Sadhu et al. |
| 2014/0378479 A1 | 12/2014 | Kesicki et al. |
| 2015/0080572 A1 | 3/2015 | Carra et al. |
| 2015/0175605 A1 | 6/2015 | Bremner et al. |
| 2015/0175606 A1 | 6/2015 | Buttar |
| 2016/0075705 A1 | 3/2016 | Kesicki et al. |
| 2016/0376274 A1 | 12/2016 | Carra et al. |
| 2017/0049772 A1 | 2/2017 | Sadhu et al. |
| 2017/0340633 A1 | 11/2017 | Chanchal et al. |
| 2018/0009811 A1 | 1/2018 | Buttar et al. |

FOREIGN PATENT DOCUMENTS

| | | |
|---|---|---|
| EP | 0 675 124 A2 | 10/1995 |
| EP | 0 716 857 A1 | 6/1996 |
| EP | 0 884 310 A1 | 12/1998 |
| EP | 0 900 568 A2 | 3/1999 |
| GB | 1 356 763 A | 6/1974 |
| GB | 2 017 097 A | 10/1979 |
| JP | S53-44581 A | 4/1978 |
| JP | 55-118917 A2 | 9/1980 |
| JP | 55-118918 A2 | 9/1980 |
| JP | 56-002322 A2 | 1/1981 |
| JP | 2003-519698 A | 6/2003 |
| JP | 2007-537291 A | 12/2007 |
| JP | 2012-524126 A | 10/2012 |
| WO | WO-93/21259 A1 | 10/1993 |
| WO | WO-94/17090 A1 | 8/1994 |
| WO | WO-95/24379 A1 | 9/1995 |
| WO | WO-96/04923 A1 | 2/1996 |
| WO | WO-96/25488 A1 | 8/1996 |
| WO | WO-96/32478 A1 | 10/1996 |
| WO | WO-97/34631 A1 | 9/1997 |
| WO | WO-97/41097 A2 | 11/1997 |
| WO | WO-97/43276 A1 | 11/1997 |
| WO | WO-97/46688 A1 | 12/1997 |
| WO | WO-98/33802 A1 | 8/1998 |
| WO | WO-98/38173 A1 | 9/1998 |
| WO | WO-99/08501 A2 | 2/1999 |
| WO | WO-99/34804 A1 | 7/1999 |
| WO | WO-01/00881 A1 | 1/2001 |
| WO | WO-01/030768 A1 | 5/2001 |
| WO | WO-01/051919 A3 | 7/2001 |
| WO | WO-01/53266 A1 | 7/2001 |
| WO | WO-01/57034 A1 | 8/2001 |
| WO | WO-01/81346 A2 | 11/2001 |
| WO | WO-03/035075 A1 | 5/2003 |
| WO | WO-03/106622 A2 | 12/2003 |
| WO | WO-2004/007491 A1 | 1/2004 |
| WO | WO-2004/012768 A1 | 2/2004 |
| WO | WO-2004/026285 A2 | 4/2004 |
| WO | WO-2004/029055 A1 | 4/2004 |
| WO | WO-2004/052373 A1 | 6/2004 |
| WO | WO-2004/056820 A1 | 7/2004 |
| WO | WO-2004/089925 A1 | 10/2004 |
| WO | WO-2004/108708 A1 | 12/2004 |
| WO | WO-2004/108709 A1 | 12/2004 |
| WO | WO-2004/108713 A1 | 12/2004 |
| WO | WO-2004/108715 A1 | 12/2004 |
| WO | WO-2005/016348 A1 | 2/2005 |
| WO | WO-2005/016349 A1 | 2/2005 |
| WO | WO-2005/067901 A2 | 7/2005 |
| WO | WO-2005/113554 A2 | 12/2005 |
| WO | WO-2005/113556 A1 | 12/2005 |
| WO | WO-2005/120511 A1 | 12/2005 |
| WO | WO-2009/058361 A1 | 5/2009 |
| WO | WO-2010/057048 A1 | 5/2010 |
| WO | WO-2010/065923 A2 | 6/2010 |
| WO | WO-2010/123931 A1 | 10/2010 |
| WO | WO-2011/156759 | 12/2011 |
| WO | WO-2013/134288 | 9/2013 |
| WO | WO-2014/023083 A1 | 2/2014 |
| WO | WO-2016/026380 A1 | 2/2016 |
| WO | WO-2013/082540 A1 | 6/2016 |

OTHER PUBLICATIONS

"Chemia Lekow", ed. E. Pawelczyk, PZWL, Warszawa 1986, see, part 1.2.2.
"Preparatyka Organiczna", ed. A.I. Vogel, WNT, Warszawa 1984, p. e.g. 83.
Abu-Duhier et al., Br. J. Haematol. (2001) 113:983-988.
Adamkiewicz, "Tumor Angiogenesis: Mechanisms" IMT Marburg—Research Group, retrieved from the internet on Apr. 13, 2004, located at: <http://www.imt.uni-marburg.de/~adamkiew/mechanism.html>, 2 pages.
Advisory Action from U.S. Appl. No. 11/596,092, dated Jul. 27, 2010.
Ager et al., J. Med. Chem. (1977) 20:379-386.
Ali et al., Nature (2004) 431:1007-1011.
Alon et al., "The molecular basis of leukocyte adhesion to and migration through vascular endothelium," Mirelman et al. (eds.), Life Sciences Open Day Book 2002, Weizmann Institute of Science, Life Sciences Department, Chapter 8, vol. 2:206-207 (2002), retrieved from the internet on Sep. 2, 2005, located at <http://www.weizmann.ac.il/Biology/open_day_2002/book/ronen_alon.pdf>, 2 pages.

(56) References Cited

OTHER PUBLICATIONS

Amendment from U.S. Appl. No. 09/841,341, filed Aug. 21, 2002.
Amendment from U.S. Appl. No. 10/027,591, filed Jun. 3, 2003.
Amendment in Response to Final Office Action from U.S. Appl. No. 11/596,092, filed Jul. 19, 2010.
Amendment in Response to Non-Final Office Action / Restriction Requirement from U.S. Appl. No. 11/884,566, filed Jun. 7, 2010.
Amendment in Response to Non-Final Office Action from U.S. Appl. No. 10/918,803, filed Oct. 1, 2008.
Amendment in Response to Non-Final Office Action from U.S. Appl. No. 10/918,803, filed Sep. 4, 2009.
Amendment in Response to Non-Final Office Action from U.S. Appl. No. 11/110,204, filed Dec. 31, 2008.
Amendment in Response to Non-Final Office Action from U.S. Appl. No. 11/110,204, filed Jun. 4, 2010.
Amendment in Response to Non-Final Office Action from U.S. Appl. No. 11/110,204, filed Sep. 4, 2009.
Amendment in Response to Non-Final Office Action from U.S. Appl. No. 11/596,092, filed Mar. 24, 2010.
Amendment in Response to Non-Final Office Action from U.S. Appl. No. 11/596,092, filed Nov. 10, 2009.
Amendment Under 37 C.F.R. § 1.111 from U.S. Appl. No. 11/129,006, filed Apr. 12, 2010.
Amendment Under 37 C.F.R. § 1.111/Restriction Requirement from U.S. Appl. No. 11/110,204, filed Apr. 10, 2008.
Amendment with Request for Continued Examination from U.S. Appl. No. 11/596,092, filed Sep. 1, 2010.
Amin et al., Circ Res (2003) 93(4):321-329.
Amine, M.S. et al. (Nov. 1998). "Uses of Quinazolin-2-[(β-Propionoyl) Isothiocyanate]-4-One as a Building Block in Synthesis of Some Heterocyclic Compounds of Expected Biological Activity," *Indian Journal of Chemistry* 37B(11):1153-1156.
Angel, Activities of Phosphoinositide Kinase-3 (PI3K) (1999) retrieved from the internet on May 22, 2003, URL: http://www.chem.csustan.edu/chem4400/SJBR/angel99.htm.
Angio World, "How Angiogenesis Complicates Psoriasis" (2001) retrieved from the internet on Apr. 13, 2004, located at <http://www.angioworld.com/psoriasis.htm>, 1 page.
Annabi et al., J. Cell. Biochem. (2004) 91:1146-1158.
Anonymous (2006). "Cardiovascular Disease: Treatment for Stroke", *Stanford Hospital & Clinics*, located at <http://www.stanfordhospital.com/healthLib/atoz/cardiac/stktreat.html>, last visited on Sep. 19, 2006, 2 pages.
Anonymous (2006). "Heart Disease", WebMD, located at <http://www.webmd.com/content/pages/9/1675_57842.htm> as retrieved on Sep. 14, 2006, 1 page.
Anonymous (2010) "Systemic Lupus Erythematosus", located at <http://www.nlm.nih.gov/medlineplus/ency/article/000435.htm>, last visited Aug. 1, 2010, 4 pages.
Anonymous (2010). "Spinal Cord Injury", located at <http://www.medicinenet.com/spinal_cord_injury/page.htm>, last visited on Aug. 1, 2010, 3 pages.
Anonymous, (2004). "NIH Heart Disease & Stroke Research: Fact Sheet", American Heart Association, located at <http://www.americanheart.org/presenter.jhtml?identifier=3010188>, last visited Feb. 17, 2004, 1 page.
Anonymous, (2010). "Multiple Sclerosis", located at <http://www.health.nytimes.com/health/guides/disease/multiple-sclerosis/overview.html>, last visited Aug. 1, 2010, 4 pages.
Aoki et al., PNAS USA (2001) 98:136-141.
Aoudjit et al., J. Immunol. (1998) 161:2333-2338.
Arcaro et al., Biochem. J. (1994) 298:517-520.
Asti et al., Pulm. Pharmacol. Ther. (2000) 13:61-69.
Ausprunk et al., Microvasc. Res. (1977) 14:53-65.
Australian Examination Report dated Nov. 29, 2016, for Australian Patent No. 2014364414 filed on Jun. 10, 2016, 5 pages.
Australian Re-Examination Report dated Sep. 3, 2015, for Australian Patent No. 2001255667, filed Apr. 24, 2001, 7 pages.
Azenabor, A.A. et al. (2006). "Macrophage Antioxidant Enyzmes Regulate Chlamydia Pneumoniaechronicity: Evidence of the Effect of Redox Balance on Host-Pathogen Relationship," *Immunobiology* 211(5):325-339.
Bader, A.G. et al. (2005). "Oncogenic P13K Deregulates Transcription and Translation," *Nature Reviews Cancer* 5(12):921-922 (abstract and introduction).
Barakat et al., Chemical Abstracts (1996) 124(21):1334.
Barakat, S.E-S. et al. (Dec. 1994). "Synthesis and CNS Depressant Activity of Some New Quinazoline Derivatives," *Az. J. Pharm. Sci.* 14:239-246.
Bardet et al., 9th Congress of the European Hematology Association Geneva Palexpo, Switzerland, Jun. 10-13, 2004, View Abstract data, Abstract nr.: 620.
Barker, Lancet (1991) 338:227-230.
Benekli et al., Blood (2002) 99:252-257.
Benekli et al., Blood (2003) 101:2940-2954.
Bennett et al., Ann. Intern. Med. (1985) 103:620-625.
Bennett et al., J. Pharmacol. Exp. Ther. (1997) 280:988-1000.
Berge, S.M. et al. (1977). "Pharmaceutical Salts," J. Pharma Sci. 66(1): 1-19.
Bergers et al., Science (1999) 284:808-812.
Bharadwaj et al., J. Immunol. (2001) 166:6735-6741.
Binetruy-Tournaire et al., EMBO J. (2000) 19:1525-1533.
Bloemen et al., Am. J. Respir. Crit. Care Med. (1996) 153:521-529.
Boehm et al., Nature (1997) 390:404-407.
Borregaard et al., Blood (1997) 89:3503-3521.
Boudewijn et al., Nature (1995) 376:599-602.
Bouscary et al., Blood (2003) 101:3436-3443.
Bouscary et al., Oncogene (2001) 20:2197-2204.
Bowes et al., Exp. Neurol. (1993) 119:215-219.
Brennan et al., Arthritis Res. (2002) 4(Suppl. 3):S177-S182.
Brown et al., 44$^{th}$ Annual Meeting of the American Society of Hematology, Philadelphia, PA, Dec. 6-10, 2002, Abstract No. 3012, p. 761A.
Brown, J. et al. (2010). "Clinical Activity in a Phase 1 Study of Cal-101, an Isoform-Selective Inhibitor of Phosphatidylinositol 3-Kinase P110Delta, in Patients with B-Cell Malignancies," *Haematologica* 95(s2):466, Abstract No. 1130.
Brunn et al., EMBO J. (1996) 15:5256-5267.
Burgering et al., Nature (1995) 376:599-602.
Butcher et al., Science (1996) 272:60-66.
Byrn, S. et al. (1995) "Pharmaceutical Solids: A Strategic Approach to Regulatory Considerations" *Pharmaceutical Research* 12(7)945-954.
Cadwallader et al., J. Immunol. (2002) 169:3336-3344.
Caira: "Crystalline Polymorphism of Organic Compounds", Topics in Current Chemistry, Springer, Berlin, DE, vol. 198, Jan. 1, 1998 (Jan. 1, 1998 ), pp. 163-208.
Cantley et al., PNAS USA (1999) 96:4240-4245.
Cantley et al., Science (2002) 296:1655-1657.
Cardone et al., Science (1998) 282:1318-1321.
Carnero et al., FEB Letters (1998) 422:155-159.
CAS Abstract, Accession No. DN 86:83505 [1977] pp. 111-118.
Cebon et al., Cancer Immun. (2003) 3:7-25.
Chang et al., Exp. Opin. Ther. Patents (2001) 11:45-59.
Chang, BioMed. Eng. Online (2003) 2:12.
Chantry et al., J. Biol. Chem. (1997) 272:19236-19241.
Chapman-Kirkland, E.S. et al. (1991). "Superoxide Anion Production From Human Neutrophils Measured with an Improved Kinetic and Endpoint Microassay," *J Immunol Meth* 142(1):95-104.
Chen et al., Blood (2000) 96:3181-3187.
Chern et al., Chem. Pharm. Bull. (1998) 46(6):928-933.
Chern et al., Chemical Abstracts (1998) 129(16):676.
Cheson, RD., Leonard, J.P., "'Monoclonal Antibody Therapy for B-Cell Non-Hodgkin's Lymphoma" The New England Journal of Medicine 2008, 359(6), p. 613-626.
Chopp et al., Stroke (1994) 25:869-876.
Choy et al., Arthritis & Rheumatism (2002) 46:3143-3150.
Clark et al., J. Neurosurg. (1991) 75:623-627.
Clavel et al., Joint Bone Spine (2003) 70:321-326.
Clayton et al., J. Exp. Med. (2002) 196:753-763.

(56) References Cited

OTHER PUBLICATIONS

Cleary, J.M. et al. (2010). "Development of Phosphoinositide-3 Kinase Pathway Inhibitors for Advanced Cancer," *Curr. Oncol. Rep.* 12:87-94.
Coligan et al., Current Protocols in Protein Science (2002) 3:15-20.
Communication pursuant to Rules 161(1) and 162 EPC dated Sep. 2, 2016, for European Patent Application No. 14827951.6, internationally filed on Dec. 18, 2014. 2 pages.
Computer Search Cart Navigator, located at <http://www.chemnavigator.com/members/CartNavigator.asp#sample1>, last visited Mar. 22, 2001, 8 pages.
Constantin et al., Immunity (2000) 13:759-769.
Cosimi et al., J. Immunol. (1990) 144:4604-4612.
Coxon, Immunity (1996) 5:653-666.
Creamer et al., Angiogenesis (2002) 5:231-236.
Cross et al., Inflamm. Res. (1999) 48:255-261.
Curnock et al., Immunology (2002) 105:125-136.
Dahia et al., Hum. Mol. Genet. (1999) 8:185-193.
Dallegri et al., Inflamm. Res. (1997) 46:382-391.
Das et al., Prog. Retin. Eye Res. (2003) 22:721-748.
Datta et al., Cell (1997) 91:231-241.
Datta et al., Genes & Dev. (1999) 13:2905-2927.
Davies et al., Biochem. J. (2000) 351:95-105.
De Benedetti et al., Clin. Exper. Reheum. (1992) 10:493-498.
Deininger et al., Blood (2000) 96:3343-3356.
Demeester et al., Transplantation (1996) 62:1477-1485.
Descamps et al., J. Immunol. (2004) 173:4953-4959.
Doggett et al., Biophys. J. (2002) 83:194-205.
Domanig, R. (1981). "Chinazolinone, 2. Mitt: Synthese und Einige Reaktionen Von 2-Azidomethyl-3-Aryl-4-Chinazolinonen," *Monatshefte fuer Chemie* 112(10):1195-1202. (English translation of abstract only).
Dorland's Illustrated Medical Dictionary (2003), retrieved Oct. 21, 2005 from Xreferplus, http://www.xreferplus.com/entry/4196914.
Downward, Nature (1995) 376:553-554.
Drakesmith et al., Immunol. Today (2000) 21:214-217.
Druker et al., New England Journal of Medicine (2001) 344:1038-1042.
Dunne et al., Blood (2002) 99:336-341.
Edwards et al., Canc. Res. (2002) 62:4671-4677.
Eichholtz et al., J. Biol. Chem. (1993) 268:1982-1986.
Ei-Fattah et al., Indian J Hetercyclic Chemistry (1995) 4:199-202.
El-Feky et al., Chemical Abstracts (1987) 106(13):650.
El-Feky et al., Chemical Abstracts (1999) 131(23):497.
El-Feky, S.A. (Aug. 1998). "Novel Quinazolinones From 2-Cyanomethyl-3-Phenyl-4(3H) Quinazolinone," *Bollettino Chimico Farmaceutico* 137(7):286-289.
El-Feky, S.A. et al. (1985). "Synthesis of Certain New Sulfur-Containing Quinazolinone Derivatives Likely to Possess CNS Depressant Action," *Egyptian Journal of Pharmaceutical Sciences* 24(1-4):39-47.
Engelman et al., Nature Reviews (2006) 7:606-619.
Environmental Protection Agency, EPA-Radiation Information (EPA's Radiation Protection Program:Information) "Ionizing Radiation Fact Sheet Series No. 1" (May 1998) Retrieved on Apr. 21, 2004: http://www.epa.gov/radiation/docs/ionize/ionize.htm.
Erbagci et al., Clin. Biochem. (2001) 34:645-650.
Estey, Cancer (2001) 92:1059-1073.
Etzioni, Pediatr. Res. (1996) 39:191-198.
European Search Report dated Jun. 6, 2013 for EP Patent Application No. 13150110.8, filed May 12, 2005, 6 pages.
European Search Report dated Mar. 29, 2011, for EP Patent Application No. 10163434.3, filed on Apr. 24, 2001, 9 pages.
Evarts, J.B. et al. (2010). "Discovery and Synthesis of CAL-101, a Potent and Selective Inhibitor of the Phosphatidylinositol 3-Kinase P110δ Isoform," Calistoga Pharmaceuticals Poster, PacifiChem International Chemistry Conference, Dec. 15-20, 2010, 1 page.
Extended European Search Report and European Search Opinion dated Oct. 8, 2015, for EP Patent Application No. 13757230.1, filed on Mar. 5, 2013, 6 pages.
Extended European Search Report dated Dec. 10, 2013, for EP Patent Application No. 13150110.8, filed May 12, 2005, 10 pages.
Faffe et al., Eur. Respir. J. (2000) 15:85-91.
Fantl et al., Ann. Rev. Biochem. (1993) 62:453-481.
Faust et al., Blood (2000) 96:719-726.
Ferrara N. and Alitalo, K. "Clinical application of angiogenic growth factors and their inhibitors," (1999) Nature Medicine 5:1359-1364.
Final Office Action from U.S. Appl. No. 10/918,803, dated Jan. 8, 2009.
Final Office Action from U.S. Appl. No. 11/129,006, dated Oct. 5, 2010.
Final Office Action from U.S. Appl. No. 11/596,092, dated May 18, 2010.
Final Office Action dated Dec. 18, 2015, for Colombian Patent Application No. 14-202.424, Internationally filed on Mar. 5, 2013, 11 pages (23 pages with translation).
Final Office Action dated Dec. 18, 2015, for Colombian Patent Application No. 15-129862, Internationally filed on Mar. 5, 2013, 11 pages (24 pages with translation).
Final Office Action dated Feb. 15, 2012, for U.S. Appl. No. 12/732,124, filed Mar. 25, 2010, 12 pages.
Final Office Action dated Feb. 26, 2016, for U.S. Appl. No. 14/092,287, filed Nov. 27, 2013, 6 pages.
Final Office Action dated Jul. 9, 2013, for U.S. Appl. No. 13/399,828, filed Feb. 17, 2012, 6 pages.
Final Office Action dated Jun. 7, 2012, for U.S. Appl. No. 11/129,006, filed May 12, 2005, 14 pages.
Final Office Action dated Oct. 24, 2011, for U.S. Appl. No. 12/732,128, filed Mar. 25, 2010, 8 pages.
First Examination Report dated Jan. 19, 2017, for New Zealand Patent Application No. 720867, Internationally filed Dec. 18, 2014.
First Examination Report dated Jun. 4, 2015, for New Zealand Patent Application No. 695440, Internationally filed on Mar. 5, 2013, 2 pages.
First Office Action dated Jul. 2, 2015, for Chinese Patent Application No. 201380011784.1, Internationally filed on May 3, 2015, 12 pages.
First Office Action dated Sep. 17, 2015, for Eurasian Patent Application No. 201491473/28, filed on Mar. 5, 2013, 2 pages, 2 pages English translation, (4 pages total).
First Preliminary Amendment from U.S. Appl. No. 12/538,748, filed Apr. 1, 2010.
Flinn, I.W. et al. (2009). "Preliminary Evidence of Clinical Activity in a Phase 1 Study of CAL-101, a Selective Inhibitor of the p110δ Isoform of Phosphatidylinositol 3-Kinase (PI3K), in Patients with Select Hematologic Malignancies," Journal of Clinical Oncology 27:156s, Abstract 3543.
Flinn, I.W. et al. (Nov. 20, 2009). "Evidence of Clinical Activity in a Phase 1 Study of CAL-101, an Oral P110Δ Isoform-Selective Inhibitor of Phosphatidylinositol 3-Kinase, in Patients with Relapsed or Refractory B-Cell Malignancies," *Blood* 114(22):380, Abstract 922.
Flinn, W. et al. (Jun. 4-7, 2009). "Preliminary Evidence of Clinical Activity in a Phase 1 Study of CAL-101, A Potent Selective Inhibitor of the P110Delta Isoform of Phosphatidylinositol 3-Kinase, in Patients with B-Cell Maglignancies," Haematologica 94(s2):303, Abstract 0744.
Folkman, Curr. Mol. Med. (2003) 3:643-651.
Folkman, Nat. Med. (1995) 1:27-31.
Foster, A.B. (1984). "Deuterium isotope effects in studies of drug metabolism," Trends Pharmacol Sci 5(12):524-527.
Fraser et al., Science (1991) 251:313-316.
Frey et al., Lancet (2008) 372(9643):1088-1099 (abstract).
Freyssinier et al., Br. J. Haematol. (1999) 106:912-922.
Fruman et al., Ann. Rev. Biochem. (1998) 67:481-507.
Fruman et al., Semin. Immunol. (2002) 14:7-18.
Furman, R.R. (Jul. 2010). "New Agents in Early Clinical Trials for CLL Therapy," *Clinical Advances in Hematology & Oncology* 8(7):475-476.
Fuwa et al. (2005) "Synthetic studies on 3-arylquinazolin-4-ones: intramolecular nucleophilic aromatic substitution reaction of

(56) References Cited

OTHER PUBLICATIONS 2-carboxamido-3-arylquinazolin-4-ones and its application to the synthesis of secondary aryl amines," Tetrahedron, 61:4297-4312.
Garcia-Barros et al., Science (2003) 300:1155-1159.
Genbank Accession No. AK040867, last updated Sep. 19, 2008, located at <http://www.ncbi.nlm.nih.gov.nuccore/26334014>, last visited on Apr. 16, 2010, 6 pages.
GenBank Accession No. AR255866, last updated Dec. 20, 2002, located at <http://www.ncbi.nlm.nih.gov.nuccore/27305059>, last visited on Apr. 16, 2010, 2 pages.
GenBank Accession No. BC035203, last updated Aug. 11, 2006, located at <http://www.ncbi.nlm.nih.gov/nuccore/23270986>, last visited on Apr. 16, 2010, 5 pages.
GenBank Accession No. NM_005026, last updated Apr. 11, 2010, located at <http://www.ncbi.nlm.nih.gov/nuccore/15654404>, last visited Apr. 16, 2010, 7 pages.
GenBank Accession No. NM_008840, last updated on Mar. 5, 2010, located at <http://www.ncbi.nlm.nih.gov/nuccore/255708435>, last visited on Apr. 16, 2010, 5 pages.
GenBank Accession No. U57843, last updated on May 9, 1997, located at <http://www.ncbi.nlm.nih.gov/nuccore/U57843>, last visited on Aug. 9, 2011, 2 pages.
GenBank Accession No. U86453, last updated on Jul. 7, 1998, located at <http://www.ncbi.nlm.nih.gov/nuccore/2317893>, last visited on Apr. 16, 2010, 3 pages.
GenBank Accession No. U86587, last updated Jul. 7, 1998, located at <http://www.ncbi.nlm.nih.gov/nuccore/2331237>, last visited on Apr. 16, 2010, 3 pages.
GenBank Accession No. XM_345606, last updated Jun. 22, 2006, located at <http://www.ncbi.nlm.nih.gov/nuccore/109475856?report=genbank>, last visited on Apr. 16, 2010, 3 pages.
GenBank Accession No. Y10055, last updated Oct. 7, 2008, located at <http://www.ncbi.nlm.nih.gov/nuccore/37496958>, last visited on Apr. 16, 2010, 3 pages.
Geng et al., Cancer Research (2001) 61:2413-19.
Geng et al., Cancer Research (2004) 64:4893-4899.
Geng et al., Cancer Research (2004) 64:8130-8133.
Gibson, (ed.), Antisense and Ribozyme Methodology, "Laboratory Companion" (1997) Table of Contents.
Gilliland et al., Blood (2002) 100:1532-1542.
Gilliland et al., Cancer Cell (2002) 1:417-420.
Gingras et al., Genes Dev. (2001) 15:2852-2864.
Gingras et al., Genes Dev. (2001) 15:807-826.
Glenjen et al., Int. J. Cancer (2002) 101:86-94.
Gorczynski et al., J. Immunol. (1994) 152:2011-2019.
Gorski et al., Cancer Research (1999) 59:3374-3378.
Gouilleux-Gruart et al., Blood (1996) 87:1692-1697.
Grant et al., Drugs of Today (2002) 38:783-791.
Green, S.J. et al. (1994). "Oxidative Metabolism of Murine Macrophages," Chapter 14, Unit 14.5 in *Current Protocols in Immunology*, vol. 3, John Wiley & Sons, Inc., pp. 14.5.1-14.5.11.
Gross et al., Science (1998) 281:703-706.
Gu et al., Mol. Cell. Biol. (2000) 20:7109-7120.
Gupta et al., Int'l J Radiation Oncology Biology Physics (2003) 56(3):846-853.
Gute et al., Mol. Cell. Biochem. (1998) 179:169-187.
Guzman et al., Blood (2001) 98:2301-2307.
Guzman et al., Proc. Natl. Acad. Sci. (USA) (2002) 99:16220-16225.
H. G. Brittain, "Polymorphism in Pharmaceutical Solids". Second Edition Informs Healthcare, NY (2009).
Hadden, Int. Immunopharmacol. (2003) 3:1061-1071.
Hallahan et al., Proc. Natl. Acad. Sci (USA) (1997) 94:6432-6437.
Halloran et al., Arthritis Rheum. (1996) 39:810-819.
Hanamoto et al., Am. J. Pathol. (2004) 164(3):997-1006.
Hannigan et al., Proc. Natl. Acad. Sci. U.S.A. (2002) 99:3603-3608.
Hardma et al. (eds.), Goodman and Gilman's The Pharmacological Basis of Therapeutics (1996) $9^{th}$ ed., pp. 11-16.
Harlan, Haematology 96, the Education Program Book of the 26th Congress of the International Society of Haematology. Singapore, 1996.
Harning et al., Transplantation (1991) 52:842-845.
Hartley et al., Cell (1995) 82:849-856.
Hartman et al., Cardiovasc. Res. (1995) 30:47-54.
Hasagawa et al., Int. Immunol. (1994) 6:831-838.
Hassan et al., Chinese Journal of Chemistry (1991) 9:262-269.
Hatsu, I.S. (May 1, 2001) No. 568, 45 pages, English translation 1 page, 46 pages total.
Hattori, H. et al. (May/Jun. 2010). "Reactive Oxygen Species as Signaling Molecules in Neutrophil Chemotaxis," *Communicative and Integrative Biology* 3(3):278-281.
He et al., Opthalmol. Vis. Sci. (1994) 35:3218-3225.
Healy et al., Hum. Reprod. Update (1998) 4:736-740.
Healy et al., Pharma. Res. (Dec. 2004) 21:2234-2246.
Heit et al., J. Cell Biol. (2002) 159:91-102.
Hellman, Cancer: Principles and Practice of Oncology (1993) 4th ed., vol. 1:248-275.
Hendrickson. (2005). Remington: The Science and Practice of Pharmacy, 21st edition, Lippincott, Williams & Wilkins, Philadelphia, PA. p. 732, Table 38-5.
Herman, S.E.M. et al. (Sep. 23, 2010). "Phosphatidylinositol 3-Kinase-δ Inhibitor CAL-101 Shows Promising Preclinical Activity in Chronic Lymphocytic Leukemia by Antagonizing Intrinsic and Extrinsic Cellular Survival Signals," *Blood* 116(12):2078-2088.
Herold et al., Cell Immunol. (1994) 157:489-500.
Higuchi, Prodrugs as Novel Delivery Systems, vol. 14, ASCD Symposium Series, and in Roche (ed.), Bioreversible Carriers in Drug Design, American Pharmaceutical Association and Pergamon Press (1987) Chapter 1, pp. 1-12.
Hilbert et al., J. Exper. Med. (1995) 182:243-248.
Hiles et al., Cell (1992) 70:419-429.
Hilmas et al., Rad. Res. (1975) 61:128-143.
Hirsch et al., Science (2000) 287:1049-1053.
Horgan et al., Am. J. Physiol. (1991) 261:H1578-H1584.
Hsieh, S.N. (2003). "Identification of PI3Kγ in Endothelial Cells and Its Involvement in Sphingosine 1-Phosphate Mediated Endothelial Cell Migration," Dissertation, Friedrick Schiller University, Jena, Germany, 104 pages.
Hu et al., Mol. Cell. Biol. (1993) 13:7677-7688.
Hu et al., Science (1995) 268:100-102.
Hunter, Cell (1995) 83:1-4.
Hussong et al., Blood (2000) 95:309-313.
Ikeda, H. et al. (Feb. 2009). "CAL-101: A Selective Inhibitor of PI3K p110δ for the Treatment of Multiple Myeloma," *Clinical Lymphoma and Myeloma* 9(Supp. 1):S98-S99.
Ikeda, H. et al. (Nov. 16, 2008). "CAL-101, a Specific Inhibitor of the p110δ Isoform of Phosphatidylinositide 3-Kinase Induces Cytotoxicity in Multiple Myeloma (MM)," *Blood* 112(11):950, Abstract No. 2753.
Ikeda, H. et al. (Sep. 2, 2010). "PI3K/p110δ is a Novel Therapeutic Target in Multiple Myeloma," *Blood* 116(9):1460-1468.
International Preliminary Report on Patentability for PCT/US2006/005621, dated Aug. 21, 2007, 8 pages.
International Preliminary Report on Patentability for PCT/US2014/071286, dated Jun. 21, 2016, internationally filed on Dec. 18, 2014, 5 pages.
International Preliminary Report on Patentability dated Jun. 21, 2016 for PCT/US2014/071297, filed on Dec. 18, 2014, 7 pages.
International Search Report for International (PCT) Patent Application Serial No. PCT/US2004/026436, dated Dec. 2, 2004.
International Search Report for International (PCT) Patent Application Serial No. PCT/US2004/026834, dated Nov. 29, 2004.
International Search Report for International (PCT) Patent Application Serial No. PCT/US2004/029561, dated May 25, 2005.
International Search Report for International (PCT) Patent Application Serial No. PCT/US2004/037860, dated May 6, 2005.
International Search Report dated Apr. 6, 2006, for PCT/US2005/016661, 5 pages.
International Search Report dated Aug. 29, 2005, for PCT Application No. PCT/US2005/016778, filed on May 12, 2005, 4 pages.

(56) References Cited

OTHER PUBLICATIONS

International Search Report dated Feb. 13, 2015 for PCT Application No. PCT/US2014/071297, filed on Dec. 18, 2014, 4 pages.
International Search Report dated Jun. 27, 2013, for PCT Patent Application No. PCT/US2013/029157, filed on Mar. 5, 2013, 4 pages.
International Search Report dated Mar. 20, 2015, for PCT/US2014/071286, internationally filed on Dec. 18, 2014, 4 pages.
International Search Report dated Sep. 15, 2006 for PCT Application No. PCT/US2006/005621, filed on Feb. 16, 2006, 4 pages.
Interview Summary from U.S. Appl. No. 10/918,825, dated Jun. 14, 2006.
Ishida-Okawara, A. et al. (Dec. 12, 1996). "Modulation of Degranulation and Superoxide Generation in Human Neutrophils by Unsaturated Fatty Acids of Odd Carbon Numbers," *BioChimica et Biophysica Acta* 1314(3):239-246.
Ismail and Sayed, Indian Journal of Chemistry (1982) 21B(5):461-462.
Ismail et al., Chemical Abstracts (1983) vol. 98, No. 1, p. 406.
Isobe et al., Science (1992) 255:1125-1127.
Johnson, M. et al. (2007). "Discovery and Optimization of a series of Quinazolinone-Derived Antagonists of CXCR3," Bioorg. Med Chem Lett. 17(12)3339-3343.
Johnson et al., Intl. J. Rad. One. Biol. Phys. (1976) 1:659-670.
Johnson et al., J. Endourol. (2003) 17:557-562.
Jordan, Nature Reviews: Drug Discovery (2003) 2:205.
Jou et al., Mol. Cell. Biol. (2002) 22:8580-8591.
Kahl, B.S. (May 2010). "Novel Agents for Non-Hodgkin Lymphoma," *Clinical Advances in Hematology & Oncology* 8(5)(Suppl. 10):10-15.
Kakimoto et al., Cell. Immunol. (1992) 142:326-337.
Kallman et al., Canc. Res. (1972) 32:483-490.
Kalusa, A. et al. (Oct. 6, 2008, e-published on Jul. 22, 2008). "An Efficient Synthesis of 2,3-Diaryl (3H)-Quinazolin-4-Ones Via Imidoyl Chlorides," *Tetrahedron Letters* 49(41):5840-5842.
Kandel et al., Exp. Cell Res. (1999) 253:210-229.
Kawaguchi, Y. et al. (2002) "Drug and Crystal Polymorphism" *Journal of Human Environmental Engineering* 4(2)310-317.
Kawasaki et al., J. Immunol. (1993) 150:1074-1083.
Kim et al., Endocrin. (2000) 141:1846-1853.
Kim, Retrieved from the Internet on Apr. 13, 2004: URL: http://www.math.umn.edu/~yjkim/biopaper/timy,html.
Kishimoto et al., Cell (1987) 50:193-202.
Klein et al., Cell. Signal. (2001) 13:335-343.
Klippel et al., Mol. Cell. Biol. (1994) 14:2675-2685.
Knall et al., Proc. Natl. Acad. Sci. (USA) (1997) 94:3052-3057.
Knight and Shokat, Chemistry and Biology (2005) 12:621-637.
Knight et al., Bioorganic & Medicinal Chemistry (Jul. 2004) 12:4749-4759.
Knoerzer et al., Toxicol. Pathol. (1997) 25:13-19.
Kolonin et al., Nature Medicine (2004) 10:625-632.
Kong et al., J. Biol. Chem. (2000) 275:36035-36042.
Kopf et al., Nature (1994) 368:339-342.
Krugmann et al., J. Biol. Chem. (1999) 274:17152-17158.
Kumar et al., Blood (2003) 101(10):3960-3968.
Kunkel et al., Circ. Res. (1996) 79:1196-1204.
Lannutti, B.J. et al. (Apr. 2009). "CAL-101, a Specific PI3K p110δ Inhibitor for the Treatment of Hematological Magliagnancies," *Proceedings of the American Association for Cancer Research* 50:1400, Abstract No. #SY32-2.
Lannutti, B.J. et al. (Nov. 16, 2008). "CAL-101, a Potent Selective Inhibitor of the p110d Isoform of Phosphatidylinositol 3-Kinase, Attenuates PI3K Signaling and Inhibitos Proliferation and Survival of Acure Lumpoblastic Leukemia in Addition to a Range of Other Hematological Malignancies," *Blood* 112(11):12, Abstract No. 16.
Lannutti, B.J. et al. (Nov. 20, 2009). "CAL-101, An Oral P110δ Selective Phosphatidylinositol-3-Kinase (PI3K) Inhibitor for the Treatment of B Cell Malignancies Inhibits PI3K Signaling, Cellular Viability and Protective Signals of the Microenvironment," *Blood* 114(22):120-121, Abstract No. 286.
Lannutti, J. et al. (2010). "Demonstration of Pharmacodynamic Target Inhibition and Chemokine Modulation in Patients with CLL Following Treatment with CAL-101, a Selective Inhibitor of the P110 Delta Isoform of PI3K," *Haematologica* 95(S2):45-46, Abstract No. 0113.
Lannutti, J. et al. (Jun. 4-7, 2009). "CAL-101, A Specific Inhibitor of the P11-Delta Isoform of Phosphatidylinositide 3-Kinase, for the Treatment of Non-Hodgkins Lymphomas," *Haematologica* 94(S2):272-273, Abstract No. 0668.
Lecoq-Lafon et al., Blood (1999) 93:2578-2585.
Lemmon et al., Trends Cell. Biol. (1997) 7:237-242.
Letter from Polish Patent Law Firm "Patpol" translating Office Action from Polish Patent Application No. P-358590, dated Feb. 27, 2008.
Li et al., Trends Biochem. Sci. (Jan. 2004) 29:32-38.
Liang et al., Molecular Cancer Therapeutics (2003) 2(4):353-360.
Liekens et al., Biochem. Pharmacol. (2001) 61:253-270.
Liu et al., J. Immunol. (Jan. 2004) 172:7-13.
Lowell et al., J. Cell Biol. (1996) 133:895-910.
Luo et al., Cancer Cell (2003) 4:257-262.
Luo et al., Leukemia (2003) 17:1-8.
Luster, N. Engl. J. Med. (1998) 338:436-445.
Madge et al., J. Biol. Chem. (2000) 275:15458-15465.
Manning et al., Mol. Cell (2002) 10:151-162.
Marchione et al. (2006). "Drugs hold promise in kidney cancer fight", located at <http://www.ledger-enquirer.com/mld/ledgerenquirer/living/health/14744763.htm>, last visited on Sep. 2, 2006, 3 pages.
Marley et al., Br. J. Haematol. (May 2004) 125:500-511.
May, S.E. et al. (Nov. 16, 2008). "CAL-101, a Selective Inhibitor of the p110δ Isoform of Phosphatidylinositol 3-Kinase, Effectively Induces Apoptosis in Primary Chronic Lumphocytic Leukemia Cells Providing a Novel Therapeutic Strategy for the Treatment of this Disease," *Blood* 112(11):1085-1086, Abstract No. 3165.
Meneses et al., Gene Ther. (2001) 8:646-648.
Milella et al., J. Clin. Invest. (2001) 108:851-859.
Miller et al., Nucleic Acids Res. (1988) 16:1215.
Moehler et al., Ann. Hematol. (2001) 80:695-705.
Moore, J. Clin. Invest. (2002) 109:313-315.
Morton, L.M., et al. "Lymphoma Incidence Patterns by WHO Subtype in the United States, 1992-2001" Blood 2006, 107(1), p. 265-276.
Moulton et al., Circ. (1999) 99:1726-1732.
Mulligan et al., J. Immunol. (1995) 154:1350-1363.
Mulligan et al., Proc. Natl. Acad. Sci. (USA) (1993) 90:11523-11527.
Nagase et al., Am. J. Respir. Crit. Care Med. (1996) 154:504-510.
Nakao et al., Leukemia (1996) 10:1911-1918.
Nakao et al., Muscle Nerve (1995) 18:93-102.
Neshat et al., Proc. Natl. Acad. Sci. (USA) (2001) 98:10314-10319.
New Zealand Office Action dated Aug. 24, 2018, for Patent Application No. 736970, filed Dec. 18, 2014, 5 pages.
Nicolaou et al. "Calicheamicin θ: A Rationally Designed Molecule with Extremely Potent and Selective DNA Cleaving Properties and Apoptosis Inducing Activity" Angew. Chem. Intl Ed. Engl, 33:183-186 (1994).
Ninomiya et al., J. Biol. Chem. (1994) 269:22732-22737.
Non Final Office Action from U.S. Appl. No. 11/596,092, dated Dec. 24, 2009.
Non-Final Office Action from U.S. Appl. No. 09/841,341, dated Apr. 25, 2002.
Non-Final Office Action from U.S. Appl. No. 10/027,591, dated Feb. 26, 2003.
Non-Final Office Action from U.S. Appl. No. 10/918,803, dated Apr. 1, 2008.
Non-Final Office Action from U.S. Appl. No. 10/918,803, dated Mar. 16, 2010.
Non-Final Office Action from U.S. Appl. No. 10/918,825, dated Nov. 7, 2005.
Non-Final Office Action from U.S. Appl. No. 11/110,204, dated Aug. 5, 2008.
Non-Final Office Action from U.S. Appl. No. 11/110,204, dated Feb. 4, 2010.

(56) References Cited

OTHER PUBLICATIONS

Non-Final Office Action from U.S. Appl. No. 11/110,204, dated Jun. 17, 2009.
Non-Final Office Action from U.S. Appl. No. 11/129,006, dated Dec. 15, 2009.
Non-Final Office Action from U.S. Appl. No. 11/596,092, dated Jun. 10, 2009.
Non-Final Office Action from U.S. Appl. No. 11/884,566, dated Aug. 3, 2010.
Non-Final Office Action dated Oct. 8, 2015, for U.S. Appl. No. 14/323,925, filed Jul. 3, 2014, 8 pages.
Non-Final Office Action dated Aug. 2, 2012, for U.S. Appl. No. 12/575,277, filed Oct. 7, 2009, 8 pages.
Non-Final Office Action dated Aug. 7, 2012, for U.S. Appl. No. 12/575,367, filed Oct. 7, 2009, 9 pages.
Non-Final Office Action dated Feb. 12, 2016 for U.S. Appl. No. 14/575,670, filed Dec. 18, 2014, 8 pages.
Non-Final Office Action dated Feb. 13, 2013 for U.S. Appl. No. 13/247,962, filed Sep. 28, 2011, 21 pages.
Non-Final Office Action dated Feb. 3, 2015, for U.S. Appl. No. 14/284,331, filed May 21, 2014, 16 pages.
Non-Final Office Action dated Jan. 20, 2012 for U.S. Appl. No. 13/163,597, filed Jun. 17, 2011, 14 pages.
Non-Final Office Action dated Jun. 25, 2014, for U.S. Appl. No. 14/049,154, filed Oct. 8, 2013, 15 pages.
Non-Final Office Action dated Jun. 25, 2014, for U.S. Appl. No. 14/049,163, filed Oct. 8, 2013, 15 pages.
Non-Final Office Action dated Jun. 26, 2013 for U.S. Appl. No. 13/765,610, filed Feb. 12, 2013, 9 pages.
Non-Final Office Action dated Jun. 28, 2011, for U.S. Appl. No. 12/732,124, filed Mar. 25, 2010, 11 pages.
Non-Final Office Action dated Mar. 1, 2013 for U.S. Appl. No. 13/399,828, filed Feb. 17, 2012, 6 pages.
Non-Final Office Action dated Mar. 25, 2013 for U.S. Appl. No. 13/728,807, filed Dec. 27, 2012, 13 pages.
Non-Final Office Action dated Mar. 30, 2017, for U.S. Appl. No. 15/392,198, filed Dec. 28, 2016, 6 pages.
Non-Final Office Action dated Nov. 16, 2015, for U.S. Appl. No. 14/092,287, filed Nov. 27, 2013, 11 pages.
Non-Final Office Action dated Oct. 17, 2011 for U.S. Appl. No. 12/732,124, filed Mar. 25, 2010, 8 pages.
Notice of Allowance dated Apr. 19, 2018, for U.S. Appl. No. 15/392,198, filed Dec. 28, 2016, 10 pages.
Notice of Allowance dated Apr. 3, 2018, for U.S. Appl. No. 15/817,044, filed Nov. 17, 2017, 8 pages.
Notice of Allowance dated Jan. 12, 2018, for U.S. Appl. No. 15/392,198, filed Dec. 28, 2016, 7 pages.
Notice of Allowance dated Jan. 19, 2018, for New Zealand Patent Application No. 720867, filed Jun. 6, 2016, 1 page.
Notice of Allowance dated Oct. 12, 2017 for Canadian Patent Application No. 2934531, 1 page.
Notice of Allowance dated Nov. 7, 2017 for Australian Patent Application No. 2014364410, 3 pages.
Notice of Allowance dated Jan. 23, 2018 for Japanese Patent Application No. 2016540660, 3 pages (Not Including English Translation).
Notice of Acceptance dated Oct. 7, 2016, for New Zealand Patent Application No. 629684, internationally filed on Mar. 5, 2013, 1 page.
Notice of Allowance from U.S. Appl. No. 09/841,341, dated Oct. 7, 2002.
Notice of Allowance from U.S. Appl. No. 10/027,591, dated Jul. 29, 2003.
Notice of Allowance from U.S. Appl. No. 10/337,192, dated Mar. 11, 2004.
Notice of Allowance from U.S. Appl. No. 10/697,912, dated Dec. 30, 2004.
Notice of Allowance dated Aug. 18, 2017, for U.S. Appl. No. 15/392,198, filed Dec. 28, 2016, 5 pages.
Notice of Allowance dated Aug. 28, 2013, for U.S. Appl. No. 12/575,277, filed Oct. 7, 2009, 6 pages.
Notice of Allowance dated Feb. 21, 2013, for U.S. Appl. No. 12/575,367, filed Oct. 7, 2009, 5 pages.
Notice of Allowance dated Feb. 21, 2014, for U.S. Appl. No. 13/765,610, filed Feb. 12, 2013, 9 pages.
Notice of Allowance dated Jul. 8, 2013 for U.S. Appl. No. 13/728,807, filed Dec. 27, 2012, 9 pages.
Notice of Allowance dated Jul. 8, 2013, for U.S. Appl. No. 13/730,256, filed Dec. 28, 2012, 9 pages.
Notice of Allowance dated Jun. 16, 2014, for U.S. Appl. No. 13/786,222, filed Mar. 5, 2013, 12 pages.
Notice of Allowance dated Jun. 26, 2012, for U.S. Appl. No. 12/732,124, filed Mar. 25, 2010, 11 pages.
Notice of Allowance dated Mar. 16, 2016, for Australian Patent Application No. 2015252058, Internationally filed on Mar. 5, 2013, 2 pages.
Notice of Allowance dated May 14, 2015, for U.S. Appl. No. 14/284,331, filed May 21, 2014, 9 pages.
Notice of Allowance dated May 20, 2013, for U.S. Appl. No. 13/730,276, filed Dec. 28, 2012, 7 pages.
Notice of Allowance dated Nov. 13, 2012, for U.S. Appl. No. 12/732,124, filed Mar. 25, 2010, 11 pages.
Notice of Allowance dated Nov. 8, 2010, for U.S. Appl. No. 11/110,204, filed Apr. 20, 2005, 6 pages.
Notice of Allowance dated Oct. 10, 2014, for U.S. Appl. No. 14/049,163, filed Oct. 8, 2013, 8 pages.
Notice of Allowance dated Oct. 18, 2013, for U.S. Appl. No. 13/765,610, filed Feb. 12, 2013, 10 pages.
Notice of Allowance dated Oct. 3, 2013, for U.S. Appl. No. 13/247,962, filed Sep. 28, 2011, 9 pages.
Notice of Allowance dated Oct. 9, 2014, for U.S. Appl. No. 14/049,154, filed Oct. 8, 2013, 8 pages.
Notice of Allowance dated Sep. 19, 2013, for U.S. Appl. No. 13/399,828, filed Feb. 17, 2012, 6 pages.
Notice of Allowance dated Sep. 28, 2016, for U.S. Appl. No. 14/575,670, filed Dec. 18, 2014, 7 pages.
Notice of Reexamination for Chinese Patent Application No. 0811654. X, dated Nov. 5, 2009; 7 pages.
Notice Prior to Examination, dated Sep. 7, 2015, for Israeli Patent Application No. 237644, Internationally filed on Mar. 5, 2013, 3 pages.
Notice Regarding Non-Compliant Amendment from U.S. Appl. No. 10/918,803, dated Nov. 19, 2009.
Notification of Reasons for Rejection for Japanese Patent Application No. 2003-537642, dated May 26, 2009, 4 pages.
Office Action dated Mar. 20, 2018, for European Application No. 14827950.8, filed Dec. 18, 2014, 3 pages.
Office Action dated Mar. 27, 2018, for New Zealand Patent Application No. 736970, filed Nov. 3, 2017, 3 pages.
Office Action dated Nov. 28, 2017, for New Zealand Patent Application No. 736970, filed Nov. 3, 2017, 5 pages.
Office Action dated May 24, 2017 for Canadian Patent Application No. 2,934,531, 4 pages.
Office Action dated Jul. 28, 2017 for European Patent Application No. 14 827 950.8, 3 pages.
Office Action dated Jun. 30, 2017 for Japanese Patent Application No. 2016-540660, 4 pages. (English translation).
Office Action dated Jan. 19, 2017 for New Zealand Patent Application No. 720867, 4 pages.
Office Action dated Aug. 12, 2015, for Pakistan Patent Application No. 1312013, Internationally filed on Mar. 5, 2013, 2 pages.
Office Action dated Jan. 27, 2015, for Vietnam Patent Application No. 1-2014-02846, Internationally filed on Mar. 5, 2013, 1 page.
Office Action for European Patent Application No. 01 928 855.4, dated Feb. 26, 2009, 3 pages.
Office Action for European Patent Application No. 01 928 855.4, dated Jul. 13, 2004, 5 pages.
Office Action for European Patent Application No. 01 928 855.4, dated Mar. 29, 2006, 6 pages.
Office Action for European Patent Application No. 01 928 855.4, dated Nov. 15, 2007, 4 pages.

(56) References Cited

OTHER PUBLICATIONS

Office Action for European Patent Application No. 02 757 407.8, dated Jan. 24, 2006, 3 pages.
Office Action for European Patent Application No. 02 757 407.8, dated Jul. 1, 2009, 2 pages.
Office Action for European Patent Application No. 02 757 407.8, dated Jun. 6, 2007, 2 pages.
Office Action for European Patent Application No. 02 757 407.8, dated Oct. 21, 2008, 3 pages.
Office Action for European Patent Application No. 02 757 407.8, dated Oct. 6, 2009, 3 pages.
Office Action for European Patent Application No. 04 810 878.1, dated Sep. 10, 2010, 4 pages.
Office Action for European Patent Application No. 04 816 855.3, dated Feb. 2, 2011, 4 pages.
Office Action for European Patent Application No. 04 816 855.3, dated Oct. 21, 2008, 4 pages.
Office Action for European Patent Application No. 05 752 122.1, dated Dec. 28, 2010, 4 pages.
Office Action for European Patent Application No. 05 752 122.1, dated Mar. 25, 2013, 4 pages.
Office Action for European Patent Application No. 05 752 122.1, dated Nov. 5, 2014, 3 pages.
Office Action dated Apr. 12, 2016, for Japanese Patent Application No. 2014-561048, Internationally filed on Mar. 5, 2013, 7 pages.
Office Action dated Jul. 14, 2015, for Colombian Patent Application No. 15-129-862, filed on Jun. 5, 2015, 9 pages, (23 pages with translation).
Office Action dated Jul. 14, 2015, for Colombian Patent Application No. 14-202 424, Internationally filed on Mar. 5, 2015, 10 pages (22 pages with translation).
Office Action dated Mar. 9, 2016, for Chinese Patent Application No. 201380011784.1, Internationally filed on Mar. 5, 2013, 12 pages.
Office Action dated Nov. 26, 2015, for Eurasian Patent Application No. 201491473/28, Internationally filed on Mar. 5, 2013, 1 page.
Ohno-Matsui et al., Invest. Ophthalmol. Vis: Sci. (2003) 44:5370-5375.
Okkenhaug et al., Science (2002) 297:1031-1034.
O'Mahony et al., (2002) "Traceless synthesis of 3H-quinazolin-4-ones yia a combination of solid-phase and solution methodologies," Tetrahedron Letters, 43:939-942.
Oppenheimer-Marks et al., J. Clin. Invest. (1998) 101:1261-1272.
Opposition dated Nov. 10, 2015, for Chilean Patent Application No. 2014-02358, Internationally filed on Mar. 5, 2013, 2 pages.
Oshima, H. (2007). "Crystallization of Polymorphs and Pseudo-Polymorphs and Its Control," Pharm Stage 6(10)48-53, English translation of the introduction with certification, 20 pages.
Oshiro et al., Stroke (1997) 28:2031-2038.
Otsu et al., Cell (1991) 65:91-104.
Paez et al., Frank (ed.), Cancer Treatment and Research (2003) 115:146 Kluwer Academic Publishers.
Pages et al., Nature (1994) 369:327-329.
Palanki, Curr. Med. Chem. (2002) 9:219-227.
Paleolog et al., Angiogenesis (1998/1999) 2:295-307.
Panayotou et al., "Phosphatidyl-inositol 3-kinase: a key enzyme in diverse signalling processes." Trends Cell BioL 2:358-60 (1992).
Panayotou et al., Trends in Cell Biol. (1992) 2:358-360.
Panes et al., Gastroenterology (1995) 108:1761-1769.
Parasharya and Parikh, J. Inst. Chemists (1992) 64(5):184-185.
Parasharya et al., Chemical Abstracts (1994) vol. 121, No. 9, p. 1065.
Park, S. et al. (2010). "Role of the PI3K/AKT and mTOR Signaling Pathways in Acute Myeloid Leukemia," *Haematologica* 95(5):819-829.
Parker et al., "PI 3-kinase puts GTP on the Rac" Curr. Biol., 5:577-79 (1995).
Passegue et al., Proc. Natl. Acad. Sci., (USA) (2003) 100 Supp. 1:11842-11849.
Patani, G.A. et al. (1996), "Bioisosterism: A Rational Approach in Drug Design," *Chem Rev.* 96(8):3147-3176.
Pierce et al., J. Biol. Chem. (1997) 272:21096-21103.
Pietersz et al, "Antibody conjugates for the treatment of cancer." Immunol. Rev., 129:57-80 (1992).
Plows et al., J. Immunol. (1999) 162(2):1018-1023.
Podsypanina et al., Proc. Natl. Acad. Sci. (USA) (2001) 98:10320-10325.
Psychoyos et al., J. Immunol. Methods (1991) 137:37-46.
Puri et al., Blood (2005) 106(1):150-157, 144.
Puri et al., Blood (May 2004) 103:3448-3456.
Puri, K. et al. (Jul. 18-23, 2004). "A Role for Phosphoinositide 3-Kinase δ in Neutrophil Trafficking," Immunology 2004: Cytokine Network, Regulatory Cells, Signaling, and Apoptosis Collection of Free Papers Presented at the 12$^{th}$ International Congress of Immunology and 4$^{th}$ Annual Conference of FOCIS Medimond International Proceedings in Montreal, Canada on Jul. 18, 23, 2004, pp. 303-307.
Quirici et al., Br. J. Haematol. (2001) 115:186-194.
Rada, B.K. et al. (Nov. 1, 2004, e-published Jul. 13, 2004). "Dual Role of Phagocytic NADPH Oxidase in Bacterial Killing," *Blood* 104(9):2947-2953.
Rameh et al. "The role of phosphoinositide 3-kinase lipid products in cell function." J. BioL Chem., 274:8347-8350 (1999).
Rameh et al., Cell (1995) 83:821-830.
Rathman et al., J. Org. Chem. (1980) 45:2169-2176.
Remington's Pharmaceutical Sciences (1990) 18th Ed., Chapter 89, pp. 1435-1712 Table of Contents Only.
Ren et al., Curr. Drug Targets Inflamm. Allergy (2003) 2(3):242-256.
Request for Continued Examination and Amendment Under 37 C.F.R. § 1.116 from U.S. Appl. No. 10/918,803, filed May 7, 2009.
Response to Election of Species Requirement from U.S. Appl. No. 10/918,803, filed Jun. 27, 2007.
Response to Non-Final Office Action filed on Sep. 16, 2010, for U.S. Appl. No. 10/918,803, filed Aug. 13, 2004, 25 pages.
Response to Non-Final Office Action from U.S. Appl. No. 10/918,803, filed Dec. 18, 2009.
Response to Restriction Requirement from U.S. Appl. No. 10/918,803, filed Jan. 4, 2008.
Response to Restriction Requirement from U.S. Appl. No. 11/129,006, filed May 12, 2009.
Response to Restriction Requirement from U.S. Appl. No. 11/137,901, filed Feb. 6, 2008.
Response to Restriction Requirement from U.S. Appl. No. 11/596,092, filed May 27, 2009.
Response to Rule 312 Communication dated Oct. 4, 2012, for U.S. Appl. No. 12/732,124, filed Mar. 25, 2010, 7 pages.
Restriction Requirement from U.S. Appl. No. 10/918,803, dated Jun. 12, 2009.
Restriction Requirement from U.S. Appl. No. 10/918,803, dated Mar. 13, 2007.
Restriction Requirement from U.S. Appl. No. 10/918,803, dated Sep. 7, 2007.
Restriction Requirement from U.S. Appl. No. 11/110,204, dated Mar. 10, 2008.
Restriction Requirement from U.S. Appl. No. 11/129,006, dated Nov. 12, 2008.
Restriction Requirement from U.S. Appl. No. 11/137,901, dated Aug. 6, 2007.
Restriction Requirement from U.S. Appl. No. 11/137,901, dated May 23, 2008.
Restriction Requirement from U.S. Appl. No. 11/596,092, dated Jan. 28, 2009.
Restriction Requirement from U.S. Appl. No. 11/884,566, dated Apr. 5, 2010.
Restriction Requirement dated Dec. 1, 2011, for U.S. Appl. No. 13/163,597, filed Jun. 17, 2011, 7 pages.
Restriction Requirement dated Feb. 3, 2014, for U.S. Appl. No. 13/786,222, filed Mar. 5, 2013, 17 pages.
Restriction Requirement dated Jul. 17, 2012, for U.S. Appl. No. 13/247,962, filed Sep. 28, 2011, 27 pages.

(56) References Cited

OTHER PUBLICATIONS

Restriction Requirement dated Jun. 7, 2012, for U.S. Appl. No. 13/399,828, filed Feb. 17, 2012, 5 pages.
Restriction Requirement dated May 8, 2015, for U.S. Appl. No. 14/092,287, filed Nov. 27, 2013, 8 pages.
Restriction Requirement dated Oct. 14, 2010, for U.S. Appl. No. 12/732,124, filed Mar. 25, 2010, 9 pages.
Restriction Requirement dated Sep. 11, 2012, for U.S. Appl. No. 13/399,828, filed Feb. 17, 2012, 7 pages.
Reyes et al., J. Clin. Invest. (2002) 109:337-346.
Rickert et al., Trends Cell Biol. (2000) 10:466-473.
Riesterer, Int'l J Radiation Oncology Biology Physics (2004) 361-368.
Roberts et al., Immunity (1999) 10:183-196.
Rodrigues et al., Mol. Cell. Biol. (2000) 20:1448-1459.
Rodriguez-Viciana et al., EMBO J. (1996) 15:2442-2451.
Roth et al., J. Immunol. Methods (1995) 188:97-116.
Rowlinson-Busza et al, "Targeted delivery of biologic and other antineoplastic agents." Curr. Opin. Oncol, 4:1142 (1992).
Rudd, "Upstream-downstream: CD28 cosignaling pathways and T cell function." Immunity, 4:527-34 (1996).
Rupnick et al., Proc. Nat'l. Acad. Sci. (USA) (2002) 99:10730-35.
Sadhu et al., J. Immunol. (2003) 170:2647-2654.
Saleh, R.M. et al. (1994). "Synthesis and Reactions of 2-(α-Phenylimido-β-O-Chlorophenyl)Vinyl-4(H)-3,1-Benzoxazin-4-One," Revue Roumaine De Chimie, 39(5):567-576.
Salven et al., Blood (1999) 94:3334-3339.
Salvesen et al., Cell (1997) 91:443-446.
Sasaki et al., Science (2000) 287:1040-1046.
Sauder et al., J. Am. Acad. Dermatol. (2002) 47:535-541.
Schimmer et al., J. Immunol. (1998) 160:1466-1471.
Schuch et al., Blood (2002) 100:4622-4628.
Schueneman et al., Canc. Res. (2003) 63:4009-4016.
Second Preliminary Amendment and Response to Notice to File Missing Parts of U.S. Appl. No. 12/575,277, filed Jan. 20, 2010.
Second Preliminary Amendment and Response to Notice to File Missing Parts of U.S. Appl. No. 12/575,367, filed Jan. 20, 2010.
Second Preliminary Amendment from U.S. Appl. No. 11/110,204, filed Aug. 24, 2007.
Second Preliminary Amendment from U.S. Appl. No. 11/884,566, filed May 13, 2008.
Sengupta et al., Circulation (2003) 107:2955-2961.
Shimamoto et al., Leukemia Res. (2003) 27:783-788.
Shiojima et al., Circ. Res. (2002) 90:1243-1250.
Shvidel et al., Hematol. J. (2002) 3:32-37.
Smith et al., Am. J. Respir. Cell Mol. Biol. (1996) 15(6):693-702.
Soliman, F.M.A. et al. (1992). "Synthesis and Reactions of Substituted Benzoxazinones Bearing a Bulky Group at Position 2," Revue Roumaine De Chimie, 37(10):1153-1158.
Song et al., Canc. Res. (1974) 34:2344-2350.
Springer, Cell (1994) 76:301-314.
Stahl, P. H. and Wermuth, C. G. (2011) Pharmaceutical Salts: Properties, Selection, and Use (International Union of Pure and Applied Chemistry), Wiley-VCH; 2nd revise Edition. Table of Contents.
Stein et al., Mol. Med. Today (2000) 6:347-357.
Stenmark et al., J. Cell. Sci. (1999) 112:4175-4183.
Stennicke et al., Biochim. Biophys. Acta. (2000) 1477:299-306.
Stephens et al., Current Biology (1994) 4:203-214.
Stirewalt et al., Nat. Rev. Cancer (2003) 3:650-665.
Stoyanov et al., Science (1995) 269:690-693.
Su et al., Cancer Research (2003) 63:3585-3592.
Sumariwalla et al., Arthritis Res. Ther. (2002) 5:R32-R39.
Sunil et al., Respir. Res. (2002) 3:21.
Supplemental Amendment from U.S. Appl. No. 11/110,204, filed Oct. 27, 2009.
Supplemental Notice of Allowance from U.S. Appl. No. 10/337,192, dated Jun. 29, 2004.

Supplementary European Search Report dated Oct. 27, 2015, for European Patent Application No. 13757230.1, Internationally filed on Mar. 5, 2013, 1 page.
Sutton, A. (Jun. 9, 2006). "Baylor, St. Luke's study uses gene therapy as pancreatic cancer", located at <http://www.bcm.edu/news/item.cfm?newsID=640>, last visited on Sep. 2, 2006, 2 pages.
Tager et al., J. Exp. Med. (2000) 192:439-446.
Takata, N. (2007) "API Form Screening and Selection in Drug Discovery Stage," Pharm Stage 6(10)20-25, English translation of the introduction with certification, 11 pages.
Takeuchi et al. (1989). "A new efficient of imidazolinones and quinazolinone by intramolecular aza—Wittig reaction," Tetrahedron, 45(20):6375-6386, Schemes 5-6.
Talento et al., Transplantation (1993) 55:418-422.
Tamiya et al., Immunopharmacology (1995) 29:53-63.
Tan et al., Cancer Research (2003) 63:7663-7667.
Tan et al., J. Immunol. Meths. (2000), 238:59-68.
Tan, J. et al. (Sep. 1, 2004). "A Specific Antagonist of the p110-Delta Catalytic Component of P13 Kinase, IC486068, Enhances Radiation-Induced Tumor Vascular Destruction," International Journal of Radiation: Oncology Biology Physics 60(1):S195.
Tanaka et al., J. Immunol. (1993) 151:5088-5095.
Tang et al., J. Biol. Chem. (1999) 274:16741-16746.
Taylor et al., Curr. Opin. Rheumatol. (2005) 17(3):293-298.
Tesar et al., Med. Sc. Monit. (2002) 8:BR24-BR29.
The Merck Manual on "arthritis" (2008).
The Merck Manual on "rheumatoid arthritis" (2008).
The Merck Manual, 17th ed, (1999) p. 1001.
Thelan et al., Proc. Natl. Acad. Sci. (USA) (1994) 91:4960-4964.
Ting et al., Int. J. Rad. Biol. (1991) 60:335-339.
Trail et al., "Cure of xenografted human carcinomas by BR96-doxorubicin immunoconjugates." Science, 261:212 (1993).
U.S. Appl. No. 15/993,299, filed May 30, 2018, by Sadhu et al. (U.S. Patent Application is not submitted herewith pursuant to the waiver of 37 C.F.R. § 1.98(a)(2)(iii) issued by the Office dated Sep. 21, 2004.).
U.S. Appl. No. 14/488,182, filed Sep. 16, 2014, by Carra et al. (U.S. Patent Application is not submitted herewith pursuant to the waiver of 37 C.F.R. § 1.98(a)(2)(iii) issued by the Office dated Sep. 21, 2004.).
Vacca et al., Blood (1999) 9:3064-3073.
Van Dijk et al., Blood (2000) 96:3406-3413.
Van Eeden, S.F. et al. (Dec. 17, 1999). "The Use of Flow Cytometry to Measure Neutrophil Function," Journal Immunol Meth 232:23-43.
Vanhaesebroeck et al., FASEB J. (1996) 10:A1395, Abst. No. 2280.
Vanhaesebroeck et al., Proc. Natl. Acad. Sci., (USA) (1997) 94:4330-4335.
Vanhaesebroeck et al., TIBS (1997) 22:267-272.
Vanparia, S.F. et al. (Feb. 12, 2013). "Synthesis and in Vitro Antimicrobial Activity of Some Newer Quinazoline-Sulfonamide Linked Hybrid Heterocyclic Entities Derived from Glycine," Med. Chem. Res. 22(12):5184-5196.
Vermes et al., J. Immunol. Meth. (1995) 184:39-51.
Vippagunta, S.R. et al. (2001). "Crystalline Solids," Advanced Drug Delivery 48:3-26.
Vivanco et al., Nat. Rev. Cancer (2002) 2:489-501.
Vlahos et al., J. Immunol. (1995) 154:2413-2422.
Volinia et al., EMBO J. (1995) 14:3339-3348.
Volinia et al., Genomics (1994) 24:472-477.
Volinia et al., Oncogene (1992) 7:789-793.
Watanabe, T. et al. (Jan. 1, 2009, e-published on Nov. 17, 2008). "Alantrypinone and its Derivatives: Synthesis and Antagonist Activity Toward Insect GABA Receptors," Bioorganic & Medicinal Chemistry, 17(1):94-110.
Webb, H.K. et al. (Apr. 2009). "CAL-101, a Potent and Selective Inhibitor of the Class 1 Phosphatidylinositol 3 Kinase (PI3K) p110δ: Preclinical Summary," Proceedings of the American Association for Cancer Research 50:894-895, Abstract No. #3703.
Wegner et al., Lung (1992) 170:267-279.
Wegner et al., Science (1990) 247:456-459.
Weiner et al., Nat. Cell Biol. (1999) 1:75-81.
Weyand et al., Arthritis & Rheumatism (2000) 43:1041-1048.

(56) References Cited

OTHER PUBLICATIONS

Wierda, W.G., "Current and Investigational Therapies for Patients with CLL" Hematology 2006, p. 285-294.
Williams et al., Chem. Biol. (2010) 17:123-134.
Williams, D.A. et al. (2002). *Foye's Principles of Medicinal Chemistry*, Lippincott, Williams & Wilkins, Baltimore MD, Fifth Edition, pp. 50 and 59-61.
Williams, Methods Mol. Med. (2004) 98:207-216.
Wolff, ed., Burger's Medicinal Chemistry and Drug Discovery, 5$^{th}$ edition (1996) vol. 1, New York: John Wiley & Sons, pp. 975-976.
Written Opinion dated Aug. 12, 2015, for Singapore Patent Application No. 11201405446P, internationally filed on Mar. 5, 2013, 5 pages.
Written Opinion dated May 27, 2015, for Singapore Patent Application No. 11201405446P, internationally filed on Mar. 5, 2013, 6 pages.
Written Opinion dated Feb. 13, 2015, for PCT/US2014/071297, filed on Dec. 18, 2014. 6 pages.
Written Opinion dated Jun. 27, 2013 for PCT Patent Application No. PCT/US2013/029157, filed on Mar. 5, 2013, 6 pages.
Written Opinion dated Mar. 20, 2015, for PCT/US2014/071286, filed on Dec. 18, 2014, 4 pages.
Wuts, P.G.M and Greene, T.W. (2006). Greene's Protective Groups in Organic Synthesis, 4th Edition, Wiley. Table of Contents.
Wymann et al., Biochem. Biophys. Acta. (1998) 1436:127-150.
Wymann et al., Biochem. J. (1994) 298:517-520.
Wymann et al., Trends Immunol. Today (2000) 21:260-264.
Xing et al., Am. J. Pathol. (1993) 143:1009-1015.
Xu et al., Blood (2003) 102:972-980.
Yamano, M. (2007) "Approach to Crystal Polymorph in Process Research of New Drug," Journal of the Society of Synthetic Organic Chemistry 65(9):907-944, English translation of the introduction with certification, 10 pages.
Yamasawa et al., Inflammation (1999) 23:263-274.
Yamaura et al., Int. J. Rad. Biol. (1976) 30:179-187.
Yao et al., Science (1995) 267:2003-2006.
Yum et al., J. Immunol. (2001) 167:6601-6608.
Zeng et al., Transplantation (1994) 58:681-689.
Zhao et al., Leukemia (2004) 18:267-75.
Zhichkin et al., (2007) "A Novel Highly Stereoselective Synthesis of 2,3-Disubstituted 3H-Quinazoline-4-one Derivatives," Organic Letters, 9(7)1415-1418.
Australian Examination Report dated Oct. 9, 2018, for Australian Patent No. 2018200461, filed Dec. 18, 2014, 3 pages.
New Zealand Office Action dated Oct. 29, 2018, for Patent Application No. 736970, filed Dec. 18, 2014, 2 pages.
Canadian Office Action dated Apr. 29, 2019, for Patent Application No. 2,934,531, filed Dec. 18, 2014, 5 pages.

PROCESS METHODS FOR PHOSPHATIDYLINOSITOL 3-KINASE INHIBITORS

CROSS REFERENCE TO RELATED APPLICATIONS

The present application is a continuation of U.S. patent application Ser. No. 15/817,044, filed Nov. 17, 2017, which is a divisional of U.S. patent application Ser. No. 15/392,198, filed Dec. 28, 2016, which is a divisional of U.S. patent application Ser. No. 14/575,670, filed Dec. 18, 2014, now U.S. Pat. No. 9,567,337, issued Feb. 14, 2017, which claims the benefit of and priority to U.S. Provisional Application Ser. No. 61/919,548, filed Dec. 20, 2013, the disclosures of which are hereby incorporated by reference in their entirety.

BACKGROUND OF THE INVENTION

The present disclosure relates generally to the synthesis or preparation of certain phosphatidylinositol 3-kinase (PI3K) inhibitors and their synthetic intermediates. Inhibitors of PI3K, such as quinazoline-purinyl containing compounds, may be useful in treating PI3K-mediated disorders such as cancer. There is a need to have alternative processes in making such PI3K inhibitors.

BRIEF SUMMARY OF THE INVENTION

The present disclosure provides a process of making certain PI3K inhibitors and compound intermediates thereof.

In one embodiment, the application discloses processes for synthesizing a compound of formula I:

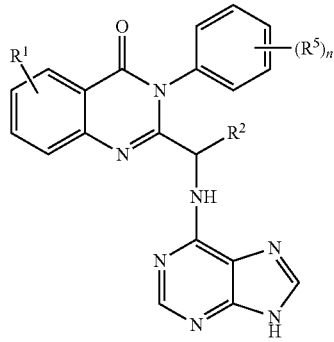

(I)

or a salt thereof.

In another embodiment, the application discloses processes for synthesizing a compound of formula II:

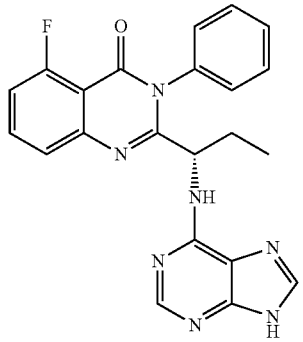

(II)

or a salt thereof.

In an alternative embodiment, the application discloses processes for synthesizing a compound of formula III:

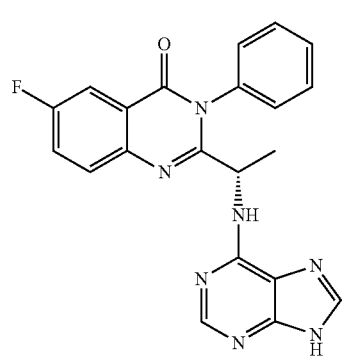

(III)

or a salt thereof.

In one embodiment, the application discloses a process for synthesizing a compound of formula 1:

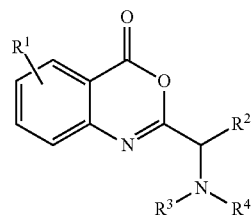

(1)

or a salt thereof, comprising step a) combining a compound of formula 2:

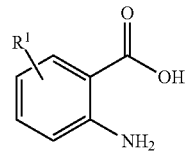

(2)

or a salt thereof, and a compound of formula 3:

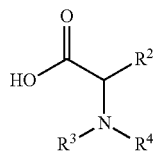
(3)

wherein the compound of formula 1 or a salt thereof is synthesized, wherein $R^1$ is halo; $R^2$ is selected from the group consisting of H and optionally substituted $C_1$-$C_8$ alkyl; and $R^3$ and $R^4$ are each independently selected from the group consisting of hydrogen, an amino protective group and an optionally substituted purinyl group.

In a further embodiment the process further comprises step b) combining the compound of formula 1 or a salt thereof; and
a compound of formula 22:

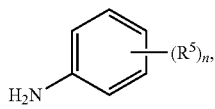
(22)

wherein n is 0-5; and each $R^5$ is independently selected from the group consisting of alkyl, alkenyl, alkynyl, carboxy, carboxyalkyl, aminocarbonyl, hydroxy, alkoxy, halogen, $CF_3$, amino, substituted amino, nitro, thiol, cyano, cycloalkyl, heterocyclyl, aryl, and heteroaryl; and
wherein a compound of formula 4:
or a salt thereof is synthesized.

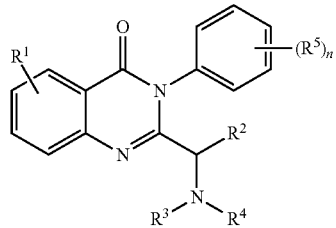
(4)

In yet a further embodiment, the process further comprises step c) combining the compound of formula 4 or a salt thereof, wherein at least one of $R_3$ and $R_4$ of the compound of formula 4 is an amino protective group; and one or more reagents, wherein the one or more reagents are used to remove the amino protective group; wherein a compound of formula 5:
or a salt thereof is synthesized;

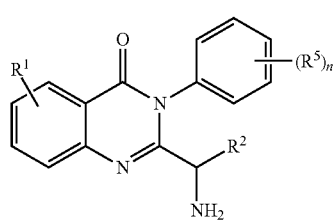
(5)

step d) combining the compound of formula 5 or a salt thereof and a compound of formula 6:

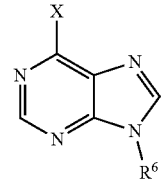
(6)

wherein X is selected from the group consisting of halogen, mesyl, mesylate, tosyl and tosylate; and $R^6$ is hydrogen or an amino protective group; wherein a compound of formula 7:

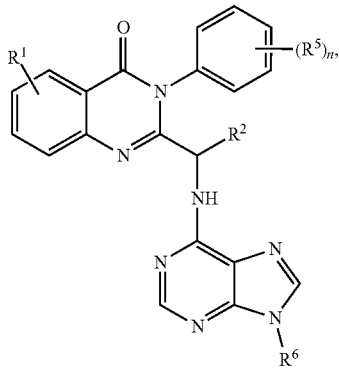
(7)

or a salt thereof is synthesized; and if $R^6$ is an amino protective group, step e) further combining the compound of formula 7 or a salt thereof; and one or more reagents, wherein the one or more reagents are used to remove the amino protective group, wherein a compound of formula I:

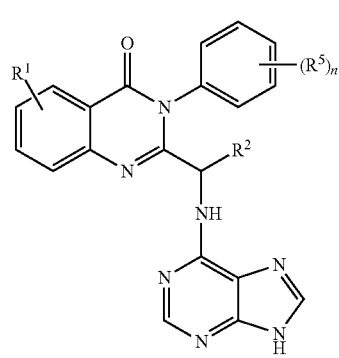
(I)

or a salt thereof is synthesized.

In one embodiment, the present application discloses a process for synthesizing a compound of formula 8:

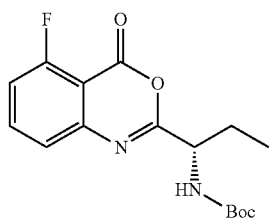 [SMILES: CC[C@H](NC(=O)OC(C)(C)C)c1nc2cccc(F)c2c(=O)o1]

(8)

or a salt thereof, comprising step a) combining a compound of formula 9

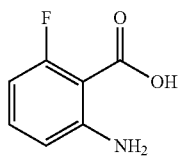

(9)

or a salt thereof, and a compound of formula 10

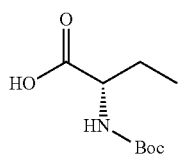

(10)

wherein the compound of formula 8 or a salt thereof is synthesized.

In a further embodiment, the process further comprises step b) combining the compound of formula 8 or a salt thereof and aniline, wherein a compound of formula 11:

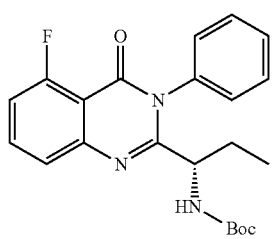 [SMILES: CC[C@H](NC(=O)OC(C)(C)C)c1nc2cccc(F)c2c(=O)n1-c1ccccc1]

(11)

or a salt thereof is synthesized.

In yet a further embodiment, the process further comprises step c) combining the compound of formula 11 or a salt thereof and an acid, wherein a compound of formula 12:

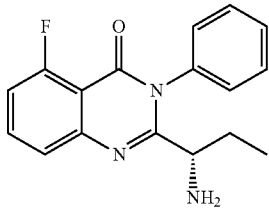 [SMILES: CC[C@H](N)c1nc2cccc(F)c2c(=O)n1-c1ccccc1]

(12)

or a salt thereof is synthesized; step d) combining the compound of formula 12 or a salt thereof and a compound of formula 13

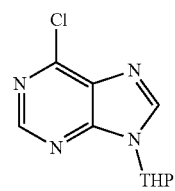

(13)

wherein a compound of formula 14:

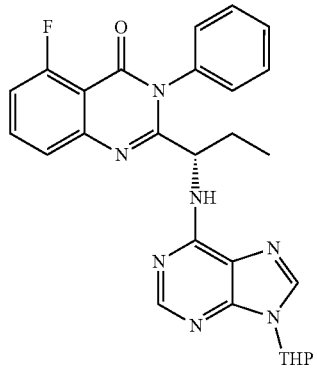

(14)

or a salt thereof is synthesized; and step e) combining the compound of formula 14 or a salt thereof and an acid, wherein a compound of formula II:

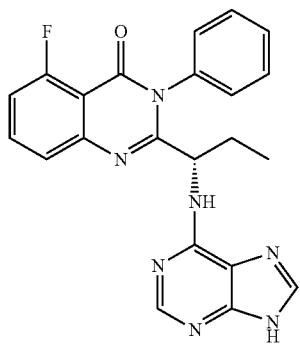

(II)

or a salt thereof is synthesized.

In an alternative embodiment, the application discloses a process for synthesizing a compound of formula 15:

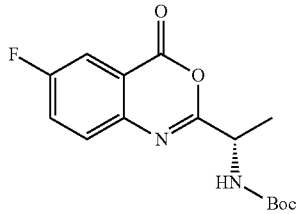
(15)

or a salt thereof, comprising step a) combining a compound of formula 16:

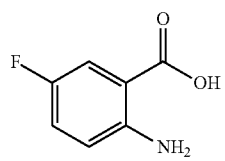
(16)

or a salt thereof,
and a compound of formula 10a:

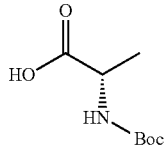
(10a)

wherein the compound of formula 15 or a salt thereof is synthesized.

In a further embodiment, the process further comprises step b) combining the compound of formula 15 or a salt thereof and aniline, wherein a compound of formula 17:

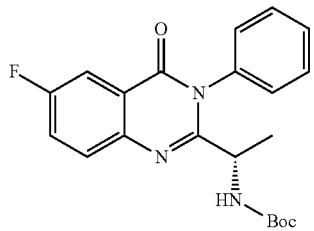
(17)

or a salt thereof is synthesized.

In yet a further embodiment, the process further comprises step c) combining the compound of formula 17 or a salt and an acid thereof, wherein a compound of formula 18:

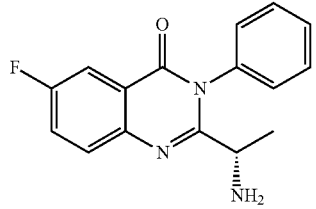
(18)

or a salt thereof is synthesized;
step d) combining the compound of formula 18 or a salt thereof and a compound of formula 13

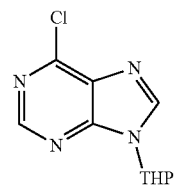
(13)

wherein a compound of formula (19):

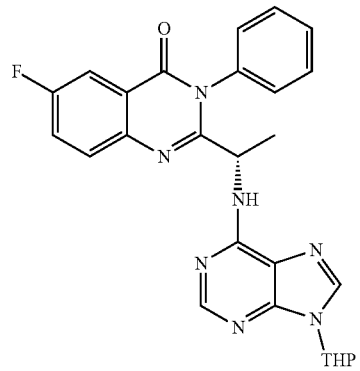
(19)

or a salt thereof is synthesized; and
step e) combining the compound of formula 19 or a salt thereof and an acid, wherein the compound of formula III:

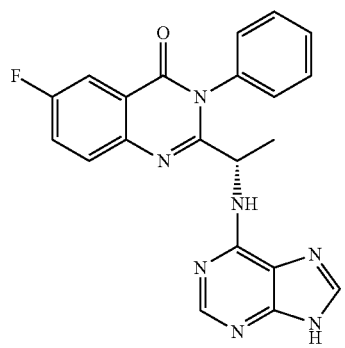
(III)

or a salt thereof is synthesized.

In some embodiments, the application discloses the intermediate compounds formed from the processes disclosed herein. In some embodiments, the application discloses compounds selected from the group consisting of (8)
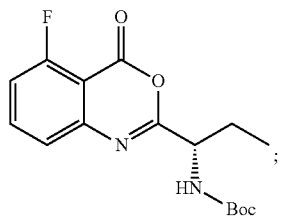

(15)
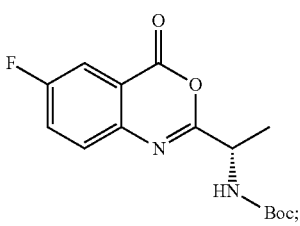

(14)
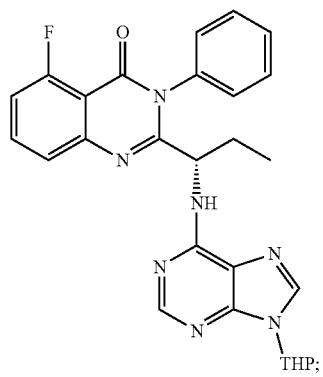

(19)
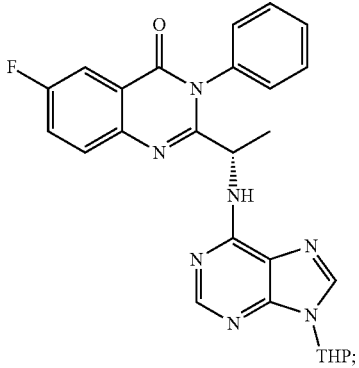

(20)
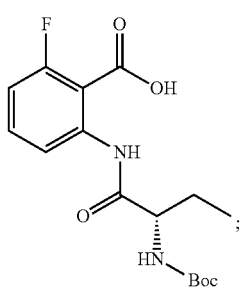

(21)
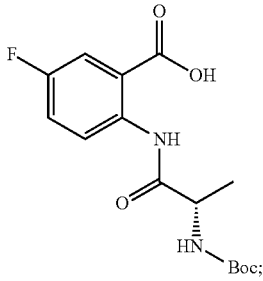

and salts thereof. In certain embodiments, compounds of formula (8), (15), (14), (19), (20), and (21), are disclosed. In certain embodiments, pharmaceutically acceptable salts of the compounds of formula (8), (15), (14), (19), (20), and (21), are disclosed.

DETAILED DESCRIPTION OF THE INVENTION

Definitions

As used in the present specification, the following words and phrases are generally intended to have the meanings as set forth below, except to the extent that the context in which they are used indicates otherwise.

The term "about" includes and describes the value or parameter per se. For example, "about x" includes and describes "x" per se. In certain embodiment, the term "about" when used in association with a measurement, or used to modify a value, a unit, a constant, or a range of values, refers to variations of +/-1-10%. In some embodiments, the term "about" when used in association with a measurement, or used to modify a value, a unit, a constant, or a range of values, refers to variations of +/-5%. In some embodiments, the term "about" when used in association with a measurement, or used to modify a value, a unit, a constant, or a range of values, refers to variations of +/-10%.

The term "between" includes and describes the value or parameter per se. For example, "between x and y" includes and describes "x" and "y" per se.

The term "and/or" includes subject matter in the alternative as well as subject matter in combination. For instance, "x, and/or y", includes "x or y" and "x and y".

The term "alkyl" as used herein refers to a straight or branched chain, saturated hydrocarbon having the indicated number of carbon atoms. For example, (C$_1$-C$_8$)alkyl is meant to include, but is not limited to methyl, ethyl, propyl, isopropyl, butyl, sec-butyl, to butyl, pentyl, isopentyl, neopentyl, hexyl, isohexyl, and neohexyl. An alkyl group can be unsubstituted or optionally substituted with one or more substituents as described herein throughout.

The term "substituted alkyl" refers to: 1) an alkyl group as defined above, having 1, 2, 3, 4 or 5 substituents, (in some embodiments, 1, 2 or 3 substituents) selected from the group consisting of alkenyl, alkynyl, carboxy, carboxyalkyl, aminocarbonyl, hydroxy, alkoxy, halogen, CF$_3$, amino, substituted amino, nitro, thiol, cyano, cycloalkyl, heterocyclyl, aryl, and heteroaryl.

The term "alkylene" refers to a diradical of a branched or unbranched saturated hydrocarbon chain, in some embodiments, having from 1 to 20 carbon atoms (e.g. 1-10 carbon atoms or 1, 2, 3, 4, 5 or 6 carbon atoms). This teen is exemplified by groups such as methylene (–CH$_2$–), ethylene (—CH$_2$CH$_2$—), the propylene isomers (e.g., —CH$_2$CH$_2$CH$_2$— and —CH(CH$_3$)CH$_2$—), and the like.

The term "substituted alkylene" refers to an alkylene group as defined above having 1 to 5 substituents (in some embodiments, 1, 2 or 3 substituents) as defined for substituted alkyl.

The term "aralkyl" refers to an aryl group covalently linked to an alkylene group, where aryl and alkylene are defined herein. "Optionally substituted aralkyl" refers to an optionally substituted aryl group covalently linked to an optionally substituted alkylene group. Such aralkyl groups are exemplified by benzyl, phenylethyl, 3-(4-methoxyphenyl)propyl, and the like.

The term "aralkyloxy" refers to the group —O-aralkyl. "Optionally substituted aralkyloxy" refers to an optionally substituted aralkyl group covalently linked to an optionally substituted alkylene group. Such aralkyl groups are exemplified by benzyloxy, phenylethyloxy, and the like.

The term "alkenyl" refers to a monoradical of a branched or unbranched unsaturated hydrocarbon group having from 2 to 20 carbon atoms (in some embodiments, from 2 to 10 carbon atoms, e.g. 2 to 6 carbon atoms) and having from 1 to 6 carbon-carbon double bonds, e.g. 1, 2 or 3 carbon-carbon double bonds. In some embodiments, alkenyl groups include ethenyl (or vinyl, i.e. —CH=CH$_2$), 1-propylene (or allyl, i.e. —CH$_2$CH=CH$_2$), isopropylene (—C(CH$_3$)=CH$_2$), and the like.

The term "substituted alkenyl" refers to an alkenyl group as defined above having 1 to 5 substituents (in some embodiments, 1, 2 or 3 substituents) as defined for substituted alkyl.

The term "alkynyl" refers to a monoradical of an unsaturated hydrocarbon, in some embodiments, having from 2 to 20 carbon atoms (in some embodiments, from 2 to 10 carbon atoms, e.g. 2 to 6 carbon atoms) and having from 1 to 6 carbon-carbon triple bonds e.g. 1, 2 or 3 carbon-carbon triple bonds. In some embodiments, alkynyl groups include ethynyl (—C≡CH), propargyl (or propynyl, i.e. —C≡CCH$_3$), and the like.

The term "substituted alkynyl" refers to an alkynyl group as defined above having 1 to 5 substituents (in some embodiments, 1, 2 or 3 substituents) as defined for substituted alkyl.

The term "hydroxy" or "hydroxyl" refers to a group —OH.

The term "alkoxy" refers to the group R—O—, where R is alkyl; and includes, by way of example, methoxy, ethoxy n-propoxy, iso-propoxy, n-butoxy, tert-butoxy, sec-butoxy, n-pentoxy, n-hexyloxy, 1,2-dimethylbutoxy, and the like.

The term "substituted alkoxy" refers to the group R—O—, where R is substituted alkyl, where substituted alkyl, substituted alkenyl and substituted alkynyl are as defined herein.

The term "cycloalkyl" refers to cyclic alkyl groups of from 3 to 20 carbon atoms having a single cyclic ring or multiple condensed rings. Such cycloalkyl groups include, by way of example, single ring structures such as cyclopropyl, cyclobutyl, cyclopentyl, cyclooctyl and the like or multiple ring structures such as adamantanyl and bicyclo[2.2.1]heptanyl or cyclic alkyl groups to which is fused an aryl group, for example indanyl, and the like, provided that the point of attachment is through the cyclic alkyl group.

The term "cycloalkenyl" refers to cyclic alkyl groups of from 3 to 20 carbon atoms having a single cyclic ring or multiple condensed rings and having at least one double bond and in some embodiments, from 1 to 2 double bonds.

The terms "substituted cycloalkyl" and "substituted cycloalkenyl" refer to cycloalkyl or cycloalkenyl groups having 1, 2, 3, 4 or 5 substituents (in some embodiments, 1, 2 or 3 substituents), selected from the group consisting of alkyl, alkenyl, alkynyl, carboxy, carboxyalkyl, aminocarbonyl, hydroxy, alkoxy, halogen, CF$_3$, amino, substituted amino, nitro, thiol, cyano cycloalkyl, heterocyclyl, aryl, and heteroaryl.

The term "aryl" refers to an aromatic carbocyclic group of 6 to 20 carbon atoms having a single ring (e.g., phenyl) or multiple rings (e.g., biphenyl) or multiple condensed (fused) rings naphthyl, fluorenyl and anthryl). In some embodiments, aryls include phenyl, fluorenyl, naphthyl, anthryl, and the like.

Unless otherwise constrained by the definition for the aryl substituent, such aryl groups can optionally be substituted with 1, 2, 3, 4 or 5 substituents (in some embodiments, 1, 2 or 3substituents), selected from the group consisting of alkyl, alkenyl, alkynyl, carboxy, carboxyalkyl, aminocarbonyl, hydroxy, alkoxy, halogen, CF$_3$, amino, substituted amino, nitro, thiol, cyano, cycloalkyl, heterocyclyl, aryl, and heteroaryl.

The term "substituted purinyl" refers to a purinyl having 1, 2, 3, 4, or 5 substituents (in some embodiments 1, 2, or 3 substituents), each independently selected from the group consisting of alkyl alkenyl, alkynyl, carboxy, carboxyalkyl, aminocarbonyl, hydroxy, alkoxy, halogen, CF$_3$, amino, substituted amino, nitro, thiol, cyano, cycloalkyl, heterocyclyl, aryl, and heteroaryl. In some embodiments, purinyl is substituted with 1, 2, or 3 substituents selected from the group consisting of methyl, ethyl, propyl, NH$_2$, and N(CH$_3$)$_2$.

The term "heterocyclyl," "heterocycle," or "heterocyclic" refers to a monoradical saturated group having a single ring or multiple condensed rings, having from 1 to 40 carbon atoms, and from 1 to 10 heteroatoms or 1 to 4 heteroatoms within the ring, each heteroatom independently selected from the group consisting of nitrogen, sulfur, phosphorus, and oxygen.

Unless otherwise constrained by the definition for the heterocyclic substituent, such heterocyclic groups can be optionally substituted with 1 to 5 substituents (in some embodiments, 1, 2 or 3 substituents), selected from the group consisting of alkyl, alkenyl, alkynyl, carboxy, carboxyalkyl, aminocarbonyl, hydroxy, alkoxy, halogen, CF$_3$, amino, substituted amino, nitro, thiol, cyano, cycloalkyl, heterocyclyl, aryl, and heteroaryl. Examples of heterocyclics include tetrahydrofuranyl, morpholino, piperidinyl, and the like.

The term "heteroaryl" refers to a group comprising single or multiple rings comprising 1 to 15 carbon atoms and 1 to 4 heteroatoms selected from oxygen, nitrogen and sulfur within at least one ring. The term "heteroaryl" is generic, to the terms "aromatic heteroaryl" and "partially saturated heteroaryl". The term "aromatic heteroaryl" refers to a heteroaryl in which at least one ring is aromatic, regardless of the point of attachment. Examples of aromatic heteroaryls include pyrrole, thiophene, pyridine, quinoline, pteridine. The term "partially saturated heteroaryl" refers to a heteroaryl having a structure equivalent to an underlying aromatic heteroaryl which has had one or more double bonds in an aromatic ring of the underlying aromatic heteroaryl saturated. Examples of partially saturated heteroaryls include dihydropyrrole, dihydropyridine, 2-oxo-1,2-dihydropyridin-4-yl, and the like.

Unless otherwise constrained by the definition for the heteroaryl substituent, such, heteroaryl groups can be optionally substituted with 1 to 5 substituents (in some embodiments, 1, 2 or 3 substituents) selected from the group consisting alkyl, alkenyl, alkynyl, carboxy, carboxyalkyl, aminocarbonyl, hydroxy, alkoxy, halogen, CF$_3$, amino, substituted amino, nitro, thiol, cyano, cycloalkyl, heterocyclyl, aryl, and heteroaryl. Such heteroaryl groups can have a single ring (e.g., pyridyl or furyl) or multiple condensed rings (e.g., indolizinyl, benzothiazole or benzothienyl). Examples of nitrogen heterocyclyls and heteroaryls include, but are not limited to pyrrole, imidazole, pyrazole, pyridine, pyrazine, pyrimidine, pyridazine, indolizine, isoindole, indole, indazole, purine, quinolizine, isoquinoline, quinoline, phthalazine, naphthylpyridine, quinoxaline, quinazolines, cinnoline, pteridine, carbazole, carboline, phenanthridine, acridine, phenanthroline, isothiazole, phenazine, isoxazole, phenoxazine, phenothiazine, imidazolidine, imidazoline, and the like as well as N-alkoxy nitrogen containing heteroaryl compounds.

The term "substituted amino" refers to the group —NRR where each R is independently selected from the group consisting of hydrogen, alkyl, cycloalkyl, aryl, heteroaryl and heterocyclyl provided that both R groups are not hydrogen. Unless otherwise constrained by the definition, substituents may optionally be further substituted by 1, 2 or 3 substituents chosen from alkyl, alkenyl, alkynyl, carboxy, carboxyalkyl, aminocarbonyl, hydroxy, alkoxy, halogen, $CF_3$, amino, substituted amino, nitro, thiol, cyano, cycloalkyl, heterocyclyl, aryl, and heteroaryl.

The term "carboxyalkyl" refers to the groups —C(O)O-alkyl or —C(O)O-cycloalkyl, where alkyl and cycloalkyl are as defined herein, and may be optionally further substituted by alkyl, alkenyl, alkynyl, carboxy, carboxyalkyl, aminocarbonyl, hydroxy, alkoxy, halogen, $CF_3$, amino, substituted amino, nitro, thiol, cyano, cycloalkyl, heterocyclyl, aryl, and heteroaryl.

The term "aminocarbonyl" refers to the group —C(O)NRR where each R is independently hydrogen, alkyl, cycloalkyl, aryl, heteroaryl, heterocyclyl or where both R groups are joined to form a heterocyclic group (e.g., morpholino). Unless otherwise constrained by the definition, all substituents may optionally be further substituted by 1, 2 or 3 substituents chosen from alkyl, alkenyl, alkynyl, carboxy, carboxyalkyl, aminocarbonyl, hydroxy, alkoxy, halogen, $CF_3$, amino, substituted amino, nitro, thiol, cyano, cycloalkyl, heterocyclyl, aryl, and heteroaryl.

The term "thiol" refers to the group —SH.

The term "halogen" or "halo" refers to fluoro, bromo, chloro and iodo.

"Optional" or "optionally" means that the subsequently described event or circumstance may or may not occur, and that the description includes instances where said event or circumstance occurs and instances in which it does not.

A "substituted" group includes embodiments in which a monoradical substituent is bound to a single atom of the substituted group (e.g. forming a branch), and also includes embodiments in which the substituent may be a diradical bridging group bound to two adjacent atoms of the substituted group, thereby forming a fused ring on the substituted group.

Where a given group (moiety) is described herein as being attached to a second group and the site of attachment is not explicit, the given group may be attached at any available site of the given group to any available site of the second group. For example, an "alkyl-substituted phenyl", where the attachment sites are not explicit, may have any available site of the alkyl group attached to any available site of the phenyl group. In this regard, an "available site" is a site of the group at which a hydrogen of the group may be replaced with a substituent.

A compound of a given formula is intended to encompass the compounds of the disclosure, and the salts, esters, isomers, tautomers, solvates, isotopes, hydrates, and prodrugs of such compounds. Additionally, the compounds of the disclosure may possess one or more asymmetric centers, and can be produced as a racemic mixture or as individual enantiomers or diastereoisomers. The number of stereoisomers present in any given compound of a given formula depends upon the number of asymmetric centers present (there are $2^n$ stereoisomers possible where n is the number of asymmetric centers). The individual stereoisomers (including individual enantiomers and diastereoisomers) as well as racemic and non-racemic mixtures of stereoisomers are encompassed within the scope of the present disclosure, all of which are intended to be depicted by the structures of this specification unless otherwise specifically indicated. Compounds of the present disclosure include separable rotational isomers, or atropisomers.

"Isomers" are different compounds that have the same molecular formula. Isomers include stereoisomers, enantiomers and diastereomers.

"Stereoisomers" are isomers that differ only in the way the atoms are arranged in space.

"Enantiomers" are a pair of stereoisomers that are non-superimposable mirror images of each other. A 1:1 mixture of a pair of enantiomers is a "racemic" mixture. The term" (±)" is used to designate a racemic mixture where appropriate.

"Diastereoisomers" are stereoisomers that have at least two asymmetric atoms, but which are not mirror-images of each other.

The absolute stereochemistry is specified according to the Cahn Ingold Prelog R S system. When the compound is a pure enantiomer, the stereochemistry at each chiral carbon may be specified by either R or S. Resolved compounds whose absolute configuration is unknown are designated (+) or (−) depending on the direction (dextro- or laevorotary) that they rotate the plane of polarized light at the wavelength of the sodium D line.

"Tautomers" are structural isomers resulting from the migration of an atom or a functional group within the same organic molecule and lead to a change in one or more of its structural skeleton, electronic density distribution, and chemical properties. It is understood that compounds disclosed herein includes tautomeric forms although not necessarily explicitly shown. In one example, purine may be represented by any of the following tautomers:

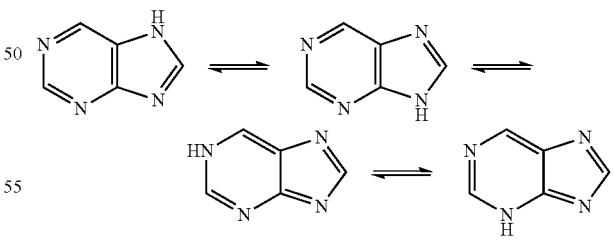

Accordingly, a reference to any one of the purine tautomers includes the other tautomeric forms.

The term "amino protective group" is well understood by the person skilled in synthetic organic chemistry as a moiety that can be selectively installed onto and removed from a suitable amine functional group. Amino protective groups, and methods for using them, are described in the authoritative treatise on the subject, P. G. M. Wuts and T. W. Greene, Greene's Protective Groups in Organic Synthesis, 4th Edition (Wiley, 2006). In some embodiments, the amino protective group is selected from the group consisting of a carbamate, an amide, and a sulfonamide. In some embodiments, the amino protective group is a benzyl group, or a Schiff base.

Non-limiting examples of carbamate based amino protective groups include methyl carbamate, 9-fluoroenylmethyl carbamate (FMOC), 2,2,2-trichloroethyl carbamate, 2-trimethylsilylethyl carbamate, 1,1-dimethylpropynyl carbamate, 1-methyl-1-phenethylc carbamate, 1-methyl-1-(4-biphenylyl)ethyl carbamate, 1,1-dimethyl-2-haloethyl carbamate, 1,1-dimethyl-2-cyanoethyl carbamate, t-butyl carbamate, cyclobutyl carbamate, 1-methylcyclobutyl carbamate; 1-adamantyl carbamate, vinyl carbamate, allyl carbamate, cinnamyl carbamate, 8-quinolyl carbamate, N-hydroxypiperidinyl carbamate, 4,5-diphenyl-3-oxazolin-2-one, benzyl carbamate, p-nitrobenzyl carbamate, 3,4-dimethoxy-6-nitrobenzyl carbamate, 2,4-dichlorobenzyl carbamate, 5-benzisoxazolylmethyl carbamate, 9-anthrylmethyl carbamate, diphenylmethyl carbamate, isonicotinyl carbamate, and S-benzyl carbamate, N—(N'-phenylaminothiocarbonyl) derivative. In one embodiment, the amino protective group is selected from the group consisting methyl carbamate, t-butyl carbamate, vinyl carbamate, and allyl carbamate. In another embodiment, the amino protective group is selected from the group consisting of t-butyl carbamate (BOC) and 9-fluoroenylmethyl carbamate (FMOC).

Non-limiting examples of amide based amino protective groups include N-formyl, N-acetyl, N-chloracetyl, N-trichloroacetyl, N-trifluoroacetyl, N-o-nitrophenylacetyl, N-o-nitrophoxyacetyl, N-acetoacetyl, N-3-phenylpropionyl, N-3-(p-hydroxyphenyl)propionyl, N-2-methyl-2-(o-nitrophenoxy)propionyl, N-4-chorobutyryl, N-o-nitrocinnamoyl, acetylmethionyl), N-benzoyl, N-phthaloyl, and N-dithiasuccinoyl. In one embodiment, the amino protective group is selected from the group consisting of N-formyl, N-acetyl, N-chloracetyl, N-trichloroacetyl, N-trifluoroacetyl, and N-acetoacetyl.

Other non-limiting examples of amino protective groups include N-allyl, N-phenacyl, N-3-acetoxypropyl, quaternary ammonium salts, N-methyoxymethyl, N-benzyloxymethyl, N-pivaloyloxymethyl, N-tetrahydropyranyl, N-2,4-dinitrophenyl, N-benzyl, N-o-nitrobenzyl, N-di(p-methoxyphenyl)methyl, N-triphenylmethyl, N-(p-methyoxyphenyl)diphenylmethyl, N-diphenyl-4-pyridylmethyl, N-2-picolyl N'-oxide, N,N'-isopropylidene, N-salicylidene, N-(5,-dimethyl-3-oxo-1-cyclohexenyl), N-nitro, N-oxide, N-diphenylphosphinyl, N-dimetylthiophosphinyl, N-dimetylthiophosphinyl, N-benzenesulfenyl, N-o-nitrobenzenesulfenyl, N-2,4,6-trimethylbenzenesulfonyl, N-toluenesulfonyl, N-benzylsulfonyl, N-trifluoromethylsulfonyl, and N-phenyacylsulfonyl. In one embodiment, the amino protective group is selected from the group consisting of N-allyl, N-phenacyl, N-3-acetoxypropyl, quaternary ammonium salts, N-methyoxymethyl, N-benzyloxymethyl, N-pivaloyloxymethyl, and N-tetrahydropyranyl. In one embodiment, the amino protective group is N-tetrahydropyranyl.

If there is a discrepancy between a depicted structure and a name given to that structure, the depicted structure controls. In addition, if the stereochemistry of a structure or a portion of a structure is not indicated with, for example, bold, wedged, or dashed lines, the structure or portion of the structure is to be interpreted as encompassing all stereo isomers of it.

The term "solvate" refers to a complex formed by the combining of a compound of any formula as disclosed herein, and a solvent.

The term "hydrate" refers to the complex formed by the combining of a compound of any formula disclosed herein, and water.

Any formula or structure given herein is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the disclosure include isotopes of hydrogen, carbon, nitrogen, oxygen, phosphorous, fluorine and chlorine, such as, but not limited to $^2$H (deuterium, D), $^3$H (tritium), $^{11}$C, $^{13}$C, $^{14}$C, $^{15}$N, $^{18}$F, $^{31}$P, $^{32}$P, $^{35}$S, $^{36}$C and $^{125}$L. Various isotopically labeled compounds of the present disclosure, for example those into which radioactive isotopes such as $^3$H, $^{13}$C and $^{14}$C are incorporated. Such isotopically labeled compounds may be useful in metabolic studies, reaction kinetic studies, detection or imaging techniques, such as positron emission tomography (PET) or single-photon emission computed tomography (SPECT) including drug or substrate tissue distribution assays or in radioactive treatment of patients.

In certain embodiments, the isotopically labeled compound is a compound of formula 6. In other embodiments, the isotopically labeled compound is a compound of formula 6, wherein X is a halogen and $R^6$ is an amino protective group. In another embodiment, the isotopically labeled compound is a compound of formula 6, wherein X is Cl and $R^6$ is THF or THP.

The disclosure also includes compounds of any formula disclosed herein, in which from 1 to "n" hydrogens attached to a carbon atom is/are replaced by deuterium, in which n is the number of hydrogens in the molecule. Such compounds may exhibit increased resistance to metabolism and may thus be useful for increasing the half-life of a compound of any formula described herein, for instance formula II or formula III, when administered to a mammal. See, for example, Foster, "Deuterium Isotope Effects in Studies of Drag Metabolism", Trends Pharmacal. Sci. 5(12):524-527 (1984). Such compounds are synthesized by means well known in the art, for example by employing starting materials in which one or more hydrogen atoms have been replaced by deuterium.

Deuterium labeled or substituted therapeutic compounds of the disclosure may have improved DMPK (drug metabolism and pharmacokinetics) properties, relating to distribution, metabolism and excretion (ADME). Substitution with heavier isotopes such as deuterium may afford certain therapeutic advantages resulting from greater metabolic stability, for example increased in vivo half-life or reduced dosage requirements. An $^{18}$F labeled compound may be useful for PET or SPECT studies. Isotopically labeled compounds of this disclosure and prodrugs thereof can generally be prepared by carrying out the procedures disclosed in the schemes or in the examples and preparations described below by substituting a readily available isotopically labeled reagent for a non-isotopically labeled reagent. Further, substitution with heavier isotopes, particularly deuterium (i.e., $^2$H or D) may afford certain therapeutic advantages resulting from greater metabolic stability, for example increased in vivo half-life or reduced dosage requirements or an improvement in therapeutic index. It is understood that deuterium in this context is regarded as a substituent in a compound of any formula disclosed herein. Similarly, in certain embodiments, tritium (i.e., $^3$H) is also regarded as a substituent in a compound of any formula disclosed herein.

In certain embodiments, $^{14}C$ is regarded as a substituent in a compound of any formula disclosed herein.

The concentration of such a heavier isotope, specifically deuterium, may be defined by an isotopic enrichment factor. In the compounds of this disclosure any atom not specifically designated as a particular isotope is meant to represent any stable isotope of that atom. Unless otherwise stated, when a position is designated specifically as "H" or "hydrogen", the position is understood to have hydrogen at its natural abundance isotopic composition. Accordingly, in the compounds of this disclosure any atom specifically designated as a deuterium (D) is meant to represent deuterium.

In many cases, the compounds of this disclosure are capable of forming acid and/or base salts by virtue of the presence of amino and/or carboxyl groups or groups similar thereto.

Base addition salts can be prepared, from inorganic and organic bases. Salts derived from in organic bases include, by way of example only, sodium, potassium, lithium, ammonium, calcium and magnesium salts. Further salts derived from organic bases include, but are not limited to, salts of primary, secondary and tertiary amines, such as alkyl amines, dialkyl amines, trialkylamines, substituted alkyl amines, di(substituted alkyl) amines, tri(substituted alkyl) amines, alkenyl amines, dialkenyl amines, trialkenyl amines, substituted alkenyl amines, disubstituted alkenyl) amines, tri(substituted alkenyl) amines, cycloalkyl amines, di(cycloalkyl) amines, tri(cycloalkyl) amines, substituted cycloalkyl amines, disubstituted cycloalkyl amine, trisubstituted cycloalkyl amines, cycloalkenyl amines, di(cycloalkenyl) amines, tri(cycloalkenyl)amines, substituted cycloalkenyl amities, disubstituted cycloalkenyl amine, trisubstituted cycloalkenyl amines, aryl amines, diaryl amines, triaryl amines, heteroaryl amines, diheteroarylamines, triheteroaryl amines, heterocyclic amines, diheterocyclic amines, triheterocyclic amines, mixed di- and tri-amines where at least two of the substituents on the amine are different and are selected from the group consisting of alkyl, substituted alkyl, alkenyl, substituted alkenyl, cycloalkyl, substituted cycloalkyl, cycloalkenyl, substituted cycloalkenyl, aryl, heteroaryl, heterocyclic, and the like. Also included are amines where the two or three substituents, together with the amino nitrogen, form a heterocyclic or heteroaryl group. In the general structure $N(R^x)(R^y)(R^z)$, mono-substituted amines have 2 of the three substituents on nitrogen ($R^x$, $R^y$ and $R^z$) as hydrogen; di-substituted amines have 1 of the three substituents on nitrogen ($R^x$, $R^y$ and $R^z$) as hydrogen; and tri-substituted amines have none of the three substituents on nitrogen ($R^x$, $R^y$ and $R^z$) as hydrogen. $R^x$, $R^y$ and $R^z$ may be selected from a variety of substituents such as hydrogen, optionally substituted alkyl, aryl, heteroaryl, cycloalkyl, cycloalkenyl, heterocyclyl and the like. The abovementioned amines refer to the compounds wherein either one, two or three substituents on the nitrogen are as listed in the name. For example, the term "cycloalkenyl amine" refers to cycloalkenyl-$NH_2$, wherein "cycloalkenyl" is as defined herein. The term "diheteroarylamine" refers to NH(heteroaryl)$_2$, wherein "heteroaryl" is as defined herein and so on.

Acid addition salts may be prepare from inorganic and organic acids. Acid addition salts may be prepared from inorganic acids such as hydrochloric acid, hydrobromic acid, sulfuric acid, nitric acid, phosphoric acid, and the like. Salts derived from organic acids include acetic acid, propionic acid, glycolic acid, pyruvic acid, oxalic acid, malic acid, malonic, acid, succinic acid, maleic acid, fumaric acid, tartaric acid, citric acid, benzoic acid, cinnamic acid, mandelic acid, methanesulfonic acid, ethanesulfonic acid, p-toluene-sulfonic acid, salicylic acid, and the like.

In some embodiments, a salt is a "pharmaceutically acceptable salt". A pharmaceutically acceptable salt of a given compound, for instance a compound of Formula I, II, or III, refers to salts that retain the biological effectiveness and properties of a given compound, and which are not biologically or otherwise undesirable. See: P. Heinrich Stahl and Camille G. Wermuth (Eds.) Pharmaceutical Salts: Properties, Selection, and Use (international Union of Pure and Applied Chemistry), Wiley-VCH; $2^{nd}$ revise Edition (May 16, 2011). In certain embodiments, a pharmaceutically acceptable salt of a given compound, for instance a compound of any of Formula I, II, or III, or a compound of any of formula 1-21, refers to that a salt form which is generally regarded as safe and suitable for use without undue toxicity, irritation, allergic response, and the like, commensurate with a reasonable benefit/risk ratio. Exemplary pharmaceutically acceptable salts include acid addition salts formed with inorganic acids such as hydrochloric acid, hydrobromic acid, sulfuric acid, nitric acid, phosphoric acid, and the like; or formed with organic acids such as acetic acid, benzenesulfonic acid, benzoic acid, camphorsulfonic acid, citric acid, ethanesulfonic acid, fumaric acid, glucoheptonic acid, gluconic acid, lactic acid, maleic acid, malonic acid, mandelic acid, methanesulfonic acid, 2-napththalenesulfonic acid, oleic acid, palmitic acid, propionic acid, stearic acid, succinic acid, tartaric acid, p-toluenesulfonic acid, trimethylacetic acid, and the like, and salts formed when an acidic proton present in the parent compound is replaced by either a metal ion, e.g., an alkali metal ion, an alkaline earth ion, or an aluminum ion; or coordinates with an organic base such as diethanolamine, triethanolamine, N-methylglucamine and the like. Also included in this definition are ammonium and substituted or quaternized ammonium salts. Representative non-limiting lists of pharmaceutically acceptable salts can be found in S. M. Berge et al., J. Pharma Sci., 66(1), 1-19 (1977), and Remington: The Science and Practice of Pharmacy, R. Hendrickson, ed., 21st edition, Lippincott, Williams Wilkins, Philadelphia, Pa., (2005), at p. 732, Table 38-5, both of which are hereby incorporated by reference herein.

Compounds described herein may be presented in the form of chemical structures or names. The compounds shown below in Table A are named using ChemBioDraw Ultra 12.0 and it should be understood that other names may be used to identify compounds of the same structure. Other compounds or radicals may be named with common names, or systematic or non-systematic names. The compounds may also be named using other nomenclature systems and symbols that are commonly recognized in the art of chemistry including, for example, Chemical Abstract Service (CAS) and International Union of Pure and Applied Chemistry (IUPAC). The naming and numbering of the compounds of the present disclosure is illustrated with the compounds shown in Table A below.

TABLE A

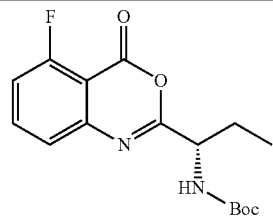

(8)

TABLE A-continued (S)-tert-butyl (1-(5-fluoro-4-oxo-4H-benzo[d][1,3]oxazin-2-yl)propyl)carbamate

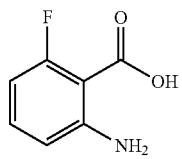
(9)

2-amino-6-fluorobenzoic acid

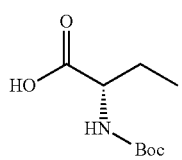
(10)

(S)-2-((tert-butoxycarbonyl)amino)butanoic acid,

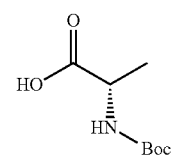
(10a)

(S)-2-((tert-butoxycarbonyl)amino)propanoic acid,

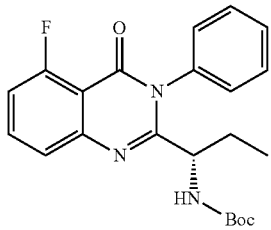
(11)

(S)-tert-butyl (1-(5-fluoro-4-oxo-3-phenyl-3,4-dihydroquinazolin-2-yl)propyl)carbamate

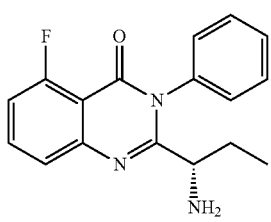
(12)

(S)-2-(1-aminopropyl)-5-fluoro-3-phenylquinazolin-4(3H)-one

TABLE A-continued

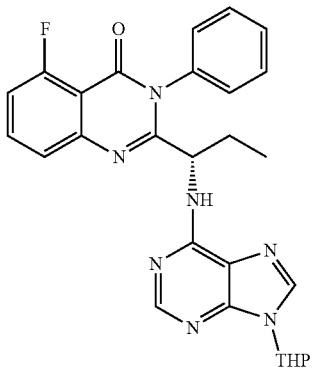
(14)

5-fluoro-3-phenyl-2-((1S)-1-((9-(tetrahydro-2H-pyran-2-yl)-9H-purin-6-yl)amino)propyl)quinazolin-4(3H)-one

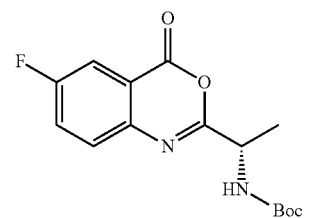 [SMILES: C[C@H](NC(=O)OC(C)(C)C)c1nc2ccc(F)cc2c(=O)o1]
(15)

(S)-tert-butyl (1-(6-fluoro-4-oxo-4H-benzo[d][1,3]oxazin-2-yl)ethyl)carbamate

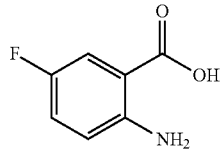 [SMILES: Nc1ccc(F)cc1C(=O)O]
(16)

2-amino-5-fluorobenzoic acid

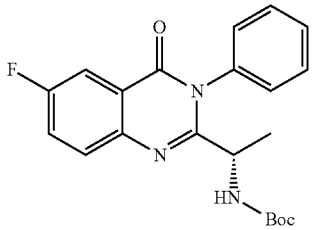 [SMILES: C[C@H](NC(=O)OC(C)(C)C)c1nc2ccc(F)cc2c(=O)n1-c1ccccc1]
(17)

(S)-tert-butyl (1-(6-fluoro-4-oxo-3-phenyl-3,4-dihydroquinazolin-2-yl)ethyl)carbamate

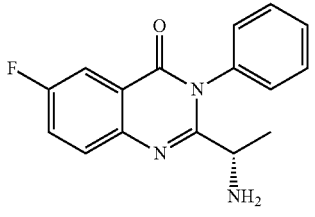
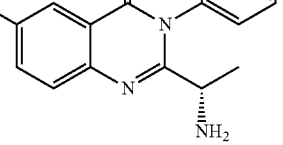
(18)

(S)-2-(1-aminoethyl)-6-fluoro-3-phenylquinazolin-4(3H)-one

TABLE A-continued (19)

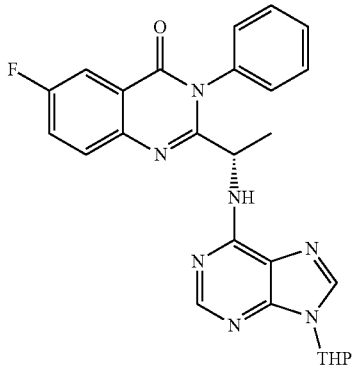

6-fluoro-3-phenyl-2-((1S)-1-((9-(tetrahydro-2H-pyran-2-yl)-9H-purin-6-yl)amino)ethyl)quinazolin-4(3H)-one (II)

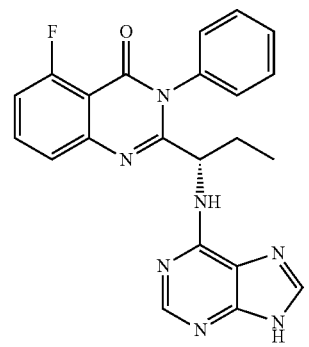 [SMILES: CC[C@H](Nc1ncnc2[nH]cnc12)c1nc2cccc(F)c2c(=O)n1-c1ccccc1]

(S)-2-(1-((9H-purin-6-yl)amino)propyl)-5-fluoro-3-phenylquinazolin-4(3H)-one (III)

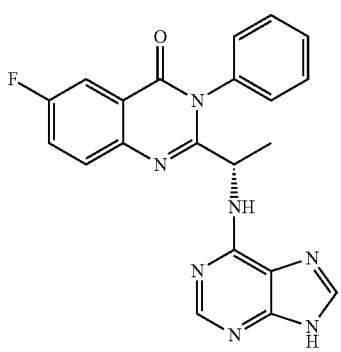 [SMILES: C[C@H](Nc1ncnc2[nH]cnc12)c1nc2ccc(F)cc2c(=O)n1-c1ccccc1]

(S)-2-(1-((9H-purin-6-yl)amino)ethyl)-6-fluoro-3-phenylquinazolin-4(3H)-one

Processes

In some embodiments, the application discloses a process for synthesizing a compound of formula 1:

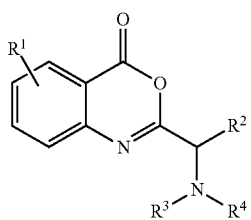
(1)

or a salt thereof, comprising step a) combining a compound of formula 2:

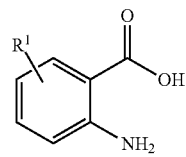
(2)

or a salt thereof,
and a compound of formula 3:

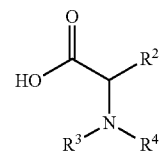
(3)

wherein the compound of formula 1 or a salt thereof is synthesized, wherein $R^1$ is halo;

$R^2$ is selected from the consisting of H, and optionally substituted $C_1$-$C_8$ alkyl; and $R^3$ and $R^4$ are each independently selected from the group consisting of hydrogen, an amino protective group and an optionally substituted purinyl group.

In some embodiments, the application discloses a process for synthesizing a compound of formula 1:

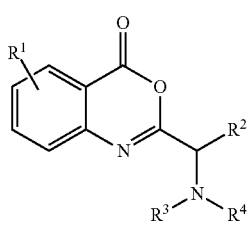
(1)

comprising step a) combining a compound of formula 2:

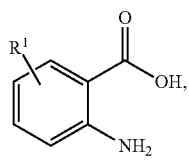

(2)

and a compound of formula 3:

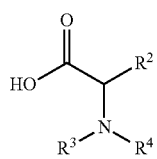

(3)

wherein the compound of formula I is synthesized,
wherein $R^1$ is halo;
$R^2$ is selected from the group consisting of H, and optionally substituted $C_1$-$C_8$ alkyl; and
$R^3$ and $R^4$ are each independently selected from the group consisting of hydrogen, an amino protective group and an optionally substituted purinyl group.

In some embodiments, $R^1$ is F or Cl. In some embodiments, $R^1$ is F. In some embodiments, $R^2$ is selected from the group consisting of methyl, ethyl or propyl. In some embodiments, $R^2$ is ethyl. In some embodiments, $R^2$ is unsubstituted $C_1$-$C_8$ alkyl. In some embodiments, $R^2$ is unsubstituted. In some embodiments, $R^3$ is H and $R^4$ is an amino protective group. In some embodiments, $R^3$ is H and $R^4$ is a carbamate. In some embodiments, $R^3$ is H and $R^4$ is an optionally substituted purinyl group. In some embodiments, $R^1$ is F or Cl; $R^2$ is selected from the group consisting of methyl, ethyl or propyl; $R^3$ is H and $R^4$ is an amino protective group. In some embodiments, $R^1$ is F or Cl; $R^2$ is selected from the group consisting of methyl, ethyl or propyl; $R^3$ is H and $R^4$ is an optionally substituted purinyl group. In some embodiments, the amino protective group is selected from the group consisting of t-butyl carbamate, tetrahydropyranyl, alkylsilyl, benzyl, an optionally substituted purinyl group, and alkoxymethyl. In other embodiments, the amino protective group is carbamate. In some embodiments, the amino protective group is t-butyl carbamate (BOC) or 9-fluoroenylmethyl carbamate (FMOC). In some embodiments, the amino protective group is BOC. In some embodiments, when $R^4$ is purinyl, the purinyl group has 0, 1, 2, 3, 4, or 5 substituents, each independently selected from the group consisting of alkyl, alkenyl, alkynyl, carboxy, carboxyalkyl, aminocarbonyl, hydroxy, alkoxy, halogen, $CF_3$, amino, substituted amino, nitro, thiol, cyano, cycloalkyl, heterocyclyl, aryl, and heteroaryl. In some embodiments, the purinyl group has 0, 1, 2, or 3 of the above list of substituents. In some embodiments, the purinyl group has 0, 1, 2, or 3 substituents selected from the group consisting of methyl, ethyl, propyl, $NH_2$, and $N(CH_3)_2$. In some embodiments, the purinyl group is has with 0, 1 or 2 substituents selected from the group consisting of methyl, ethyl, propyl, $NH_2$, and $N(CH_3)_2$. In some embodiments, the purinyl group has 1 substituent selected from the group consisting of methyl, ethyl, propyl, $NH_2$, and $N(CH_3)_2$. In some embodiments, the purinyl group is unsubstituted.

In some embodiments, step a) farther comprises a step of combining a dehydrating agent. In some embodiments, step a) (i.e., combining a compound of formula 2 or a salt thereof and a compound of formula 3 or a salt thereof) is performed in the presence of a dehydrating agent. Non-limiting examples of the dehydrating agent include DPP (diphenylphosphite), TPP (triphenylphosphite), DCC (N,N-dicyclohexylcarbodiimide), EDC (N-(3-dimethylaminopropyl)-N'-ethylcarbodiimide hydrochloride), and CDI (1,1'-carbonyldiimidazole). In some embodiments, the dehydrating agent is DPP (diphenylphosphite), TPP (triphenylphosphite), DCC (N,N'-dicyclohexylcarbodiimide), EDC (N-(3-dimethylaminopropyl)-N'-ethylcarbodiimide hydrochloride), CDI (1,1'-carbonyldiimidazole), or a mixture thereof. In some embodiments, the dehydrating agent is DPP. In some embodiments, step a) further comprises combining DPP. In some embodiments, step a) is performed in the presence of DPP.

In some embodiments, the dehydrating reagent is combined with a compound of formula 2 and a compound of formula 3, wherein the amount of the dehydrating reagent is in at least 2, 2.5, 3, 3.5, or 4 molar equivalents with respect to a compound of formula 2. In one embodiment, at least 2 molar equivalents of the dehydrating reagent with respect to the compound of formula 2 is combined with the compound of formula 2 and a compound of formula 3. In a another embodiment, at least 2 molar equivalents of the DPP (diphenylphosphite) with respect to the compound of formula 2 is combined with the compound of formula 2 and a compound of formula 3. In a yet another embodiment, at least 2 molar equivalents of the DPP (diphenylphosphite) with respect to the compound of formula 9 is combined with the compound of formula 9 and a compound of formula 10, In a further embodiment, at least 2 molar equivalents of the DPP (diphenylphosphite) with respect to the compound of formula 16 is combined with the compound of formula 16 and a compound of formula 10a.

In some embodiments, step a) further comprises a step of combining a base. In some embodiments, step a) (i.e., combining a compound of formula 2 or a salt thereof and a compound of formula 3 or a salt thereof) is performed in the presence of a base. Non-limiting examples of the base includes pyridine, 4-dimethylaminopyridine, triethylamine, isopropylethylamine, imidazole, DABCO, DBU, 2,6-lutidine, and N,N-diisopropylethylamine. In some embodiments, the base is pyridine, 4-dimethylaminopyridine, triethylamine, isopropylethylamine, imidazole, DABCO, DBU, 2,6-lutidine, N,N-thisopropylethylamine, or a mixture thereof. In some embodiments, the base is pyridine.

In some embodiments, step a) further comprises a solvent selected from the group consisting of pyridine, toluene, tetrahydrofuran, acetonitrile and 2-MeTHF. In some embodiments, step a) further comprises a solvent selected from the group consisting of pyridine, toluene, tetrahydrofuran, acetonitrile, 2-MeTHF, and a mixture thereof.

In some embodiments, step a) includes combining a compound of formula 2 or a salt thereof and a compound of formula 3 or a salt thereof with a dehydrating agent, a base, a solvent, or a mixture thereof. In some embodiments, step a) includes combining a compound of formula 2 or a salt thereof and a compound of formula 3 or a salt thereof with a dehydrating agent. In some embodiments, step a) includes combining a compound of formula 2 or a salt thereof and a compound of formula 3 or a salt thereof with a dehydrating agent and a base. In some embodiments, step a) includes combining a compound of formula 2 or a salt thereof and a compound of formula 3 or a salt thereof with a dehydrating agent, a base, and a solvent.

In some embodiments, step a) is performed at a temperature between 0 and 45 degrees Celsius, between 15 and 40 degrees Celsius, or between 20 and 30 degrees Celsius. In some embodiments, step a) is performed at a temperature below 45 degrees Celsius.

In some embodiments, the process further comprises step b) combining the compound of formula 1 or a salt thereof; and
a compound of formula 22:

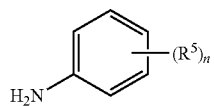

(22)

wherein n is 0-5; and each $R^5$ is independently selected from the group consisting of alkyl, alkenyl, alkynyl, carboxy, carboxyalkyl, aminocarbonyl, hydroxy, alkoxy, halogen, $CF_3$, amino, substituted amino, nitro, thiol, cyano, cycloalkyl, heterocyclyl, aryl, and heteroaryl; and
wherein a compound of formula 4:

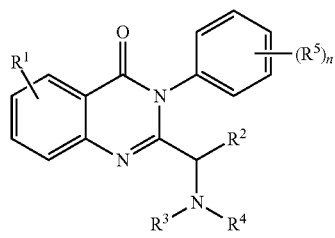

(4)

or a salt thereof is synthesized.

In some embodiments, the process further comprises step b) combining the compound of formula 1; and a compound of formula 22:

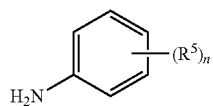

(22)

wherein n is 0-5; and each $R^5$ is independently selected from the group consisting of alkyl, alkenyl, alkynyl, carboxy, carboxyalkyl, aminocarbonyl, hydroxy, alkoxy, halogen, $CF_3$, amino, substituted amino, nitro, thiol, cyano, cycloalkyl, heterocyclyl, aryl, and heteroaryl; and
wherein a compound of formula 4:

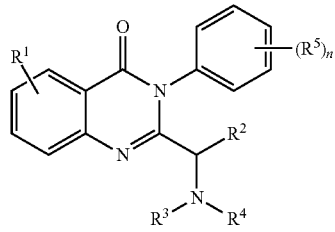

(4)

is synthesized.

In some embodiments, the compound of formula 22 is a substituted aniline. In some embodiments, n is 1-5, and in other embodiments, n is 1-3. In some embodiments n is 0-3. In some embodiments n is 0, 1, or 2. In some embodiments n is 0. In some embodiments, each $R^5$ is independently selected from the group consisting of alkyl, alkenyl, alkynyl, carboxy, carboxyalkyl, aminocarbonyl, hydroxy, alkoxy, halogen, $CF_3$, amino, substituted amino, nitro, thiol, cyano, cycloalkyl, heterocyclyl, aryl, and heteroaryl. In some embodiments, each $R^5$ is independently $C_1$-$C_4$-alkyl or halo. In other embodiments, n is 1, 2, or 3; and $R^5$ is selected from a group consisting of alkyl and halo. In some embodiments, n is 1, 2, or 3; and each $R^5$ is independently selected from a group consisting of $C_1$-$C_4$-alkyl or halo. In yet other embodiments, n is 1, 2, or 3; and $R^5$ is selected from a group consisting of methyl, F, and Cl. In some embodiments, n is 1, 2, or 3; and each $R^5$ is independently selected from a group consisting of methyl, F, and Cl. In some embodiments, the compound of formula 22 is 2,6-difluoroaniline.

In some embodiments, step b) is performed at a temperature between 0 and degrees Celsius; between 20 and 70 degrees Celsius; between 40 and 60 degrees Celsius; or between 45 and 55 degrees Celsius.

In some embodiments, the process further comprises step e) combining the compound of formula 4 or a salt thereof, wherein at least one of $R_3$ and $R_4$ of the compound of formula 4 is an amino protective group; and
one or more reagents, wherein the one or more reagents are used to remove the amino protective group; wherein a compound of formula 5:

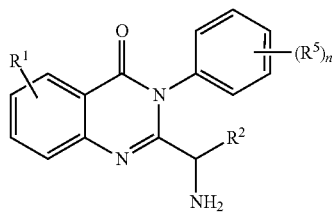

(5)

or a salt thereof is synthesized.

In some embodiments, the process further comprises step e) combining the compound of formula 4, wherein at least one of $R_3$ and $R_4$ of the compound of formula 4 is an amino protective group; and
one or more reagents, wherein the one or more reagents are used to remove the amino protective group; wherein a compound of formula 5:

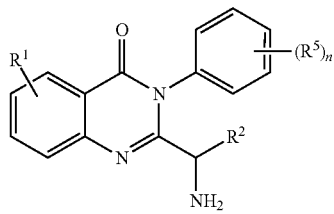

(5)

or a salt thereof is synthesized.

In some embodiments, the process further comprises step c) combining the compound of formula 4, wherein at least one of $R_3$ and $R_4$ of the compound of formula 4 is an amino protective group; and two or more reagents, wherein one of the one or more reagents is used to remove the amino protective group and wherein another of the one or more reagents is an acid; wherein a compound of formula 5:

(5)

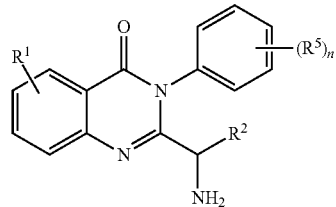

or a salt thereof is synthesized.

In some embodiments, the acid is hydrochloric acid.

In some embodiments, the process further comprises step d) combining the compound of formula 5 or a salt thereof and a compound of formula 6:

(6)

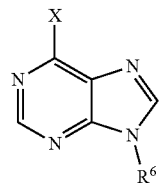

wherein X is selected from the group consisting of halogen, mesyl, mesylate, tosyl and tosylate; and $R^6$ is hydrogen or an amino protective group; wherein a compound of formula 7:

(7)

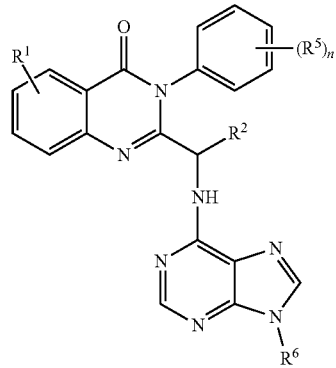

or a salt thereof is synthesized.

In some embodiments, the process further comprises step d) combining the compound of formula 5 or a salt thereof and a compound of formula 6:

(6)

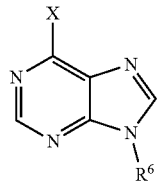

wherein X is selected from the group consisting of halogen, mesyl, mesylate, tosyl and tosylate; and $R^6$ is hydrogen or an amino protective group; herein a compound of formula 7:

(7)

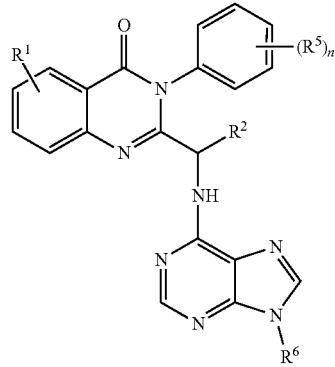

is synthesized.

In some embodiments, the process further comprises step c) combining the compound of formula 4 or a salt thereof, wherein at least one of $R_3$ and $R_4$ of the compound of formula 4 is an amino protective group; and one or more reagents, wherein the one or more reagents are used to remove the amino protective group; wherein a compound of formula 5:

(5)

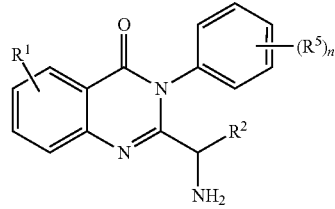

or a salt thereof is synthesized; and step d) combining the compound of formula 5 or a salt thereof and a compound of formula 6:

(6)

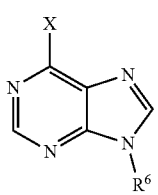

wherein X is selected from the group consisting of halogen, mesyl, mesylate, tosyl and tosylate; and R⁶ is hydrogen or an amino protective group; wherein a compound of formula 7:

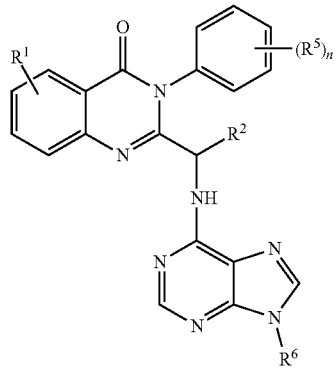

(7)

or a salt thereof is synthesized.

In some embodiments, the process further comprises step e) combining the compound of formula 4, wherein at least one of and R₄ of the compound of formula 4 is an amino protective group; and one or more reagents, wherein the one or more reagents are used to remove the amino protective group; wherein a compound of formula 5:

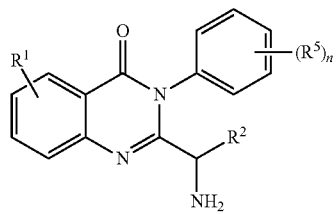

(5)

or a salt thereof is synthesized; and step d) combining the compound of formula 5 or a salt thereof and a compound of formula 6:

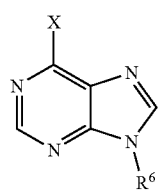

(6)

wherein X is selected from the group consisting of halogen, mesyl, mesylate, tosyl and tosylate; and R⁶ is hydrogen or an amino protective group; wherein a compound of formula 7:

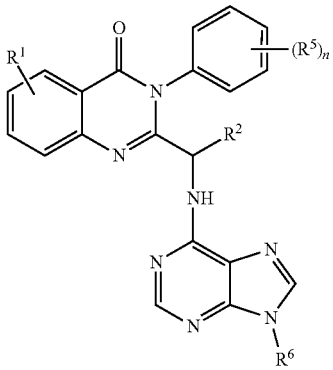

(7)

is synthesized.

In some embodiments, the compound of formula (5) is a salt. In some embodiments, the compound of formula (5) is an HCl salt.

In some embodiments, the compound of formula (7) is a salt. In some embodiments, the compound of formula (7) is an HCl salt.

In some embodiments, X is halogen. In other embodiments, X is Cl or Br. In other embodiments, X is Cl.

In some embodiments, step c) further comprises combining a solvent selected from the group consisting of acetonitrile, methanol, ethanol, isopropanol, n-propanol THF, water, and toluene. In some embodiments, step c) is performed in the presence of a solvent selected from the group consisting of acetonitrile, methanol, ethanol, isopropanol, n-propanol THF, water, toluene and mixtures thereof.

In some embodiments, step c) comprises combining one or more reagents for the deprotection of amino protective groups. For instance, if the amino protective group is an alkoxymethyl or a carbamate, such as a t-butyl carbamate or Fmoc, then the one or more reagents is an acid. In further embodiments, the acid is a mineral acid. Non-limiting examples of mineral acids include hydrochloric acid (HCl), nitric acid (HNO₃), phosphoric acid (H₃PO₄), sulfuric acid (H₂SO₄), boric acid (H₃BO₃), hydrofluoric acid (HF), hydrobromic acid (HBr), and perchloric acid (HClO₄). In some embodiments, the reagent is hydrochloric acid (HCl), nitric acid (HNO₃), phosphoric acid (H₃PO₄), sulfuric acid (H₂SO₄), boric acid (H₃BO₃), hydrofluoric acid (HF), hydrobromic acid (HBr), perchloric acid (HClO₄), or a mixture thereof. In other embodiments, the acid is trifluoroacetic acid (TFA). In another example, if the amino protective group is an alkyl silyl group, the one or more reagents are tetra-n-butylammonium fluoride (TBAF) and/or trifluoroacetic acid (TFA). In yet another example, if the amino protective group is benzyl, then the one or more reagents are Pd/C and H₂.

In some embodiments, step c) is performed at a temperature between 0 and 70 degrees Celsius; between 20 and 60 degrees Celsius; or between 35 and 50 degrees Celsius.

In some embodiments, the compound of formula 5 is synthesized as the free base, whereas in other embodiments, the compound of formula 5 is synthesized as a salt. In one embodiment, the compound of formula 5 is the salt of the compound of formula 12. In another embodiment, the compound of formula 12 is synthesized as the HCl salt. In yet other embodiments, the compound of formula 12 is synthesized as free base. In additional embodiments, the compound of formula 5 is the free base of the compound of formula 18, In some other embodiments, the compound of formula 5 is the salt of the compound of formula 18. By way of example, preparation of the salt can be followed by a neutralization step to synthesize the free base.

The choice of synthesizing either a salt or free base form may depend on the materials physical properties. In one embodiment, for stability reasons and manufacturing reasons, such as ease of handling, the compound of formula 12 is synthesized and/or isolated as the salt. In another example, the compound of formula 18 is synthesized and/or isolated as the free base, which is sufficiently stable and easy to handle.

In some embodiments, the compound of formula 5 or a salt thereof is crystallized from one or more solvents independently selected from the group comprising water, methanol, ethanol, isopropanol, n-propanol, concentrated NH$_4$OH, acetonitrile, (tert-butyl methyl ether), DCM (dichloromethane), EtOAc (ethyl acetate), iPrOAc (isopropylacetate), toluene, 2-Me-THF, DIPE (diisopropylether), heptane and heptanes. In some embodiments, the compound of formula 5 or a salt thereof is crystallized from one or more solvents selected from the group consisting of water, NH$_4$OH, acetonitrile, isopropanol, toluene, and mixtures thereof. In one embodiment, the one or more solvents are i) water, NH$_4$OH, and acetonitrile; or ii) isopropanol and toluene.

In some embodiments, step d) comprises a step of combining a base selected from the group consisting of triethylamine, pyridine, Hunig's base, and a carbonate base. In some embodiments, step d) comprises a step of combining a base selected from the group consisting of triethylamine, pyridine, Hunig's base, a carbonate base, and combinations thereof.

In some embodiments, step d) further comprises combining a solvent selected from the group consisting of water, an alcoholic solvent, and combinations thereof.

In some embodiments, step d) includes combining the compound of formula 5 or a salt thereof and a compound of formula 6 with a base or a solvent. In some embodiments, step d) includes combining the compound of formula 5 or a salt thereof and a compound of formula 6 with a base. In some embodiments, step d) includes combining the compound of formula 5 or a salt thereof and a compound of formula 6 with a solvent. In some embodiments, step d) includes combining the compound of formula 5 or a salt thereof and a compound of formula 6 with a base and a solvent.

In some embodiments, step d) is performed at a temperature between 35 and 110 degrees Celsius; between 40 and 90 degrees Celsius; between 50 and 80 degrees Celsius; or between 60 and 90 degrees Celsius.

In some embodiments, the compound of formula 7 or a salt thereof is crystallized from one or more solvents selected from the group consisting of alcohol and water. In other embodiments, the one or more solvents are methanol and water; ii) ethanol and water; iii) propanol and water; or iv) isopropanol and water.

In some embodiments, the compound of formula 6 is an unprotected purinyl compound, wherein R$^6$ is hydrogen. In alternative embodiments, the compound of formula 6 is a protected purinyl compound wherein R$^6$ is an amino protecting group. Use of the protected purinyl compound, such as the compound of formula 13, to synthesize a compound of formula 7 or a salt thereof has been observed to proceed faster, with less dipurine adducts, and at a higher yield compared to use of an unprotected purinyl compound.

In one embodiment, if R$^6$ is an amino protective group, the process further comprises step e) combining the compound of formula 7, or a salt thereof, and one or more reagents, wherein the one or more reagents are used to remove the amino protective group, wherein a compound of formula I:

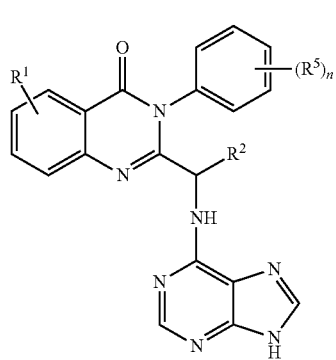

(I)

or a salt thereof is synthesized. In one embodiment, R$^6$ is an amino protective group.

In one embodiment, if R$^6$ is an amino protective group, the process further comprises step e) combining the compound of formula 7, or a salt thereof, and one or more reagents, wherein the one or more reagents are used to remove the amino protective group, wherein a compound of formula I:

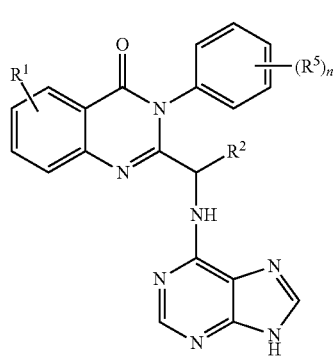

(I)

is synthesized.

As noted above, in certain embodiments, step c) comprises combining one or more reagents for the deprotection of amino protective groups. For instance, if the amino protective group is an alkoxymethyl or a carbamate, such as a t-butyl carbamate or Fmoc, then the one or more reagents is an acid. In further embodiments, the acid is a mineral acid. Non-limiting examples of mineral acids include hydrochloric acid (HCl), nitric acid (HNO$_3$), phosphoric acid (H$_3$PO$_4$), sulfuric acid (H$_2$SO$_4$), boric acid (H$_3$BO$_3$), hydrofluoric acid (HF), hydrobromic acid (HBr), and perchloric acid (HClO$_4$). In some embodiments, the reagent is hydrochloric acid (HCl), nitric acid (HNO$_3$), phosphoric acid (H$_3$PO$_4$), sulfuric acid (H$_2$SO$_4$), boric acid (H$_3$BO$_3$), hydrofluoric acid (HF), hydrobromic acid (HBr), perchloric acid (HClO$_4$), or a mixture thereof. In other embodiments, the acid is trifluoroacetic acid (TFA). In another example, if the amino protective group is an alkyl silyl group, the one or more reagents are tetra-n-butylammonium fluoride (TBAF) and/or trifluoroacetic acid (TFA). In yet another example, if the amino protective group is benzyl, then the one or more reagents are Pd/C and In yet further embodiments $R^6$ is THP (tetrahydropyranyl). In some embodiments, $R^6$ is THP and the one or more reagents used to remove the amino protective group is an acid. It has been discovered that non-aqueous acidic reaction conditions help avoid undesirable reactions such as degradation and formation of ring-opening side products. In some embodiments, the acid is generated in situ. In some embodiments, removal of the THP protective group proceeds to completion or near completion in the absence of water. In one embodiment, removal of the THP protective group proceeds to completion or near completion under anhydrous conditions. In another embodiment, removal of the THP protective group proceeds to completion or near completion with less than 0.5% water present. In a further embodiment, the acid is generated in situ. For example, ethanol and acetyl chloride may be used to generate HCl in situ. In some embodiments, step e) comprises an acid selected from the group consisting of a mineral acid, TFA and a Lewis acid. In some embodiments the acid is HCl. In another embodiment, $R^6$ is methyl 2-trimethylsilylethyl ether (SEM) and the one or more reagents used to remove the protective group is a fluoride ion.

Deprotection is considered near completion when at least 90%, 95%, 97%, 98%, 99%, 99.% or 99.9% of the protected material is deprotected.

In some embodiments, step e) is performed at a temperature between 30 and 70 degrees Celsius; between 40 and 60 degrees Celsius; or between 25 and 50 degrees Celsius.

In some embodiments, the compound of formula I or a salt thereof is crystallized from one or more solvents selected from the group comprising water, ethanol, methanol, isopropanol, n-propanol and acetone. In other embodiments, the one or more solvents are i) water; ii) ethanol; iii) acetone; iv) water and ethanol; or v) water, ethanol and acetone.

In some of the foregoing embodiments, the compound of formula 1 is

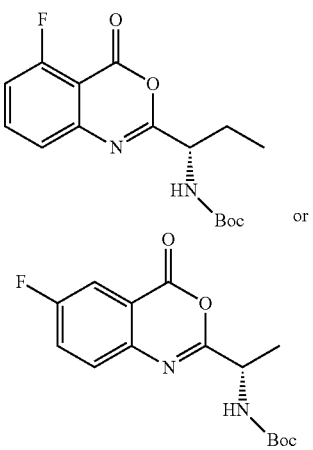

or a salt thereof.

In some of the foregoing embodiments, the compound of formula 1 is

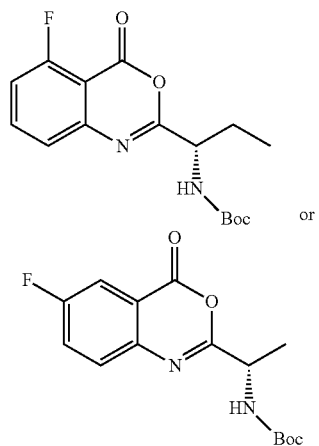

or a pharmaceutically acceptable salt thereof.

In some of the foregoing embodiments, the compound of formula 1 is

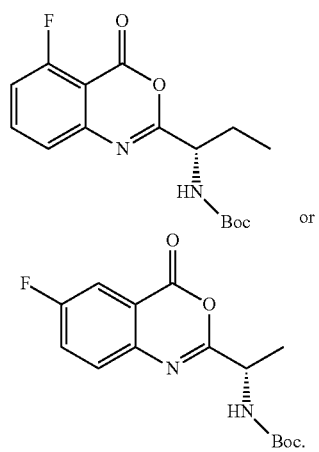

In some of the foregoing embodiments, the compound of formula 2 is

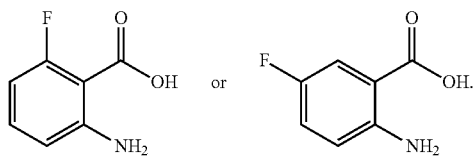 [SMILES: Nc1cccc(F)c1C(=O)O ; Nc1ccc(F)cc1C(=O)O]

In some of the foregoing embodiments, the compound of formula 3 is

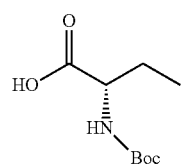

In some of the foregoing embodiments, the compound of formula 4 is

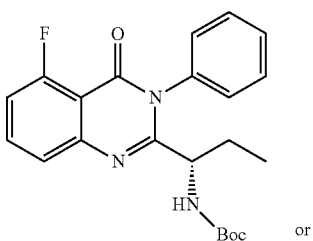

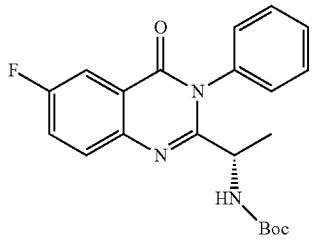

or a salt thereof.

In some of the foregoing embodiments, the compound of formula 4 is

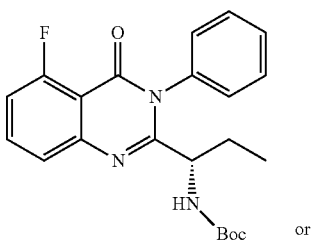

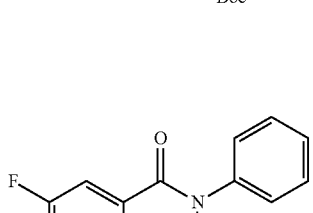

or a pharmaceutically acceptable salt thereof.

In some of the foregoing embodiments, the compound of formula 4 is

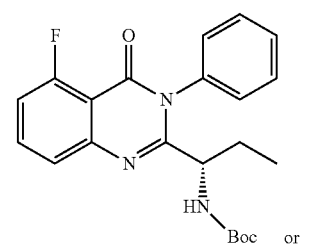

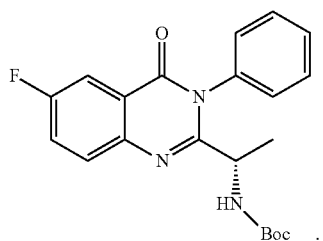

In some of the foregoing embodiments, the compound of formula 5 is

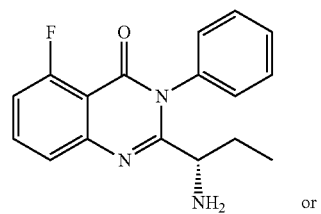

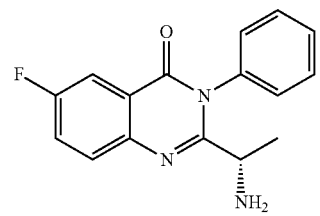

or a salt thereof.

In some of the foregoing embodiments, the compound of formula 5 is

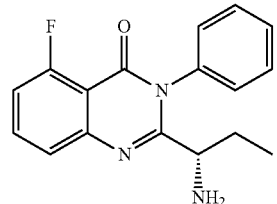

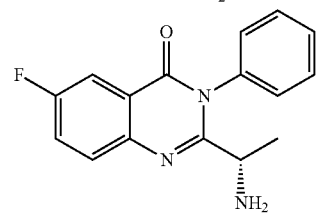

or a pharmaceutically acceptable salt thereof.

In some of the foregoing embodiments, the compound of formula 5 is

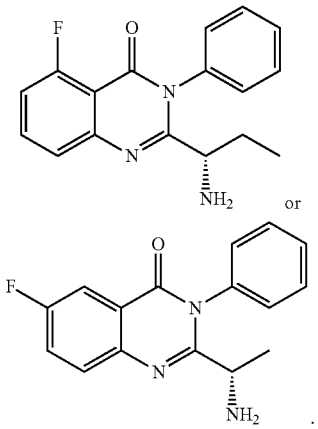

In some of the foregoing embodiments, the compound of formula 6 is

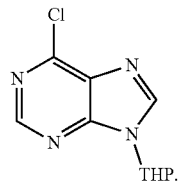

In some of the foregoing embodiments, the compound of formula 7 is

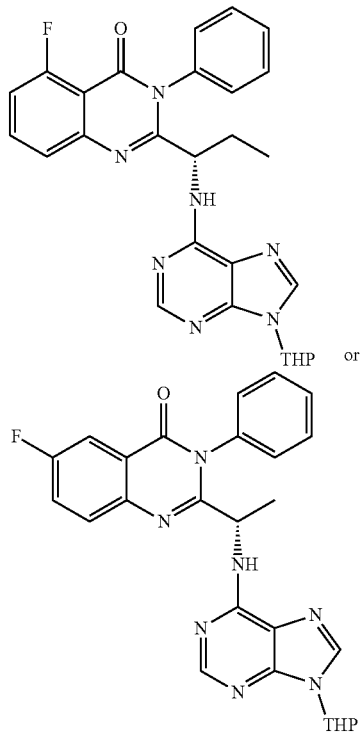

or a salt thereof.

In some of the foregoing embodiments, the compound of formula 7 is

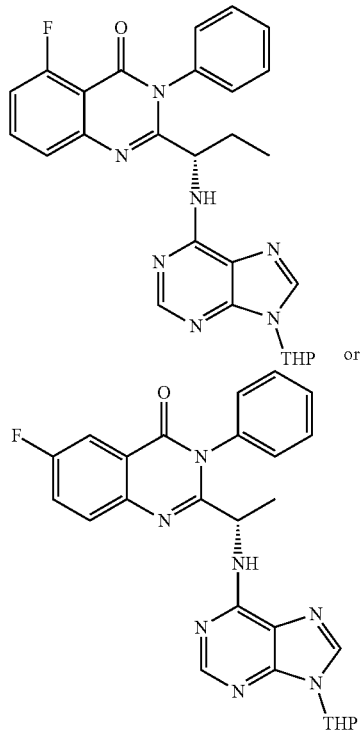

or a pharmaceutically acceptable salt thereof.

In some of the foregoing embodiments, the compound of formula 7 is

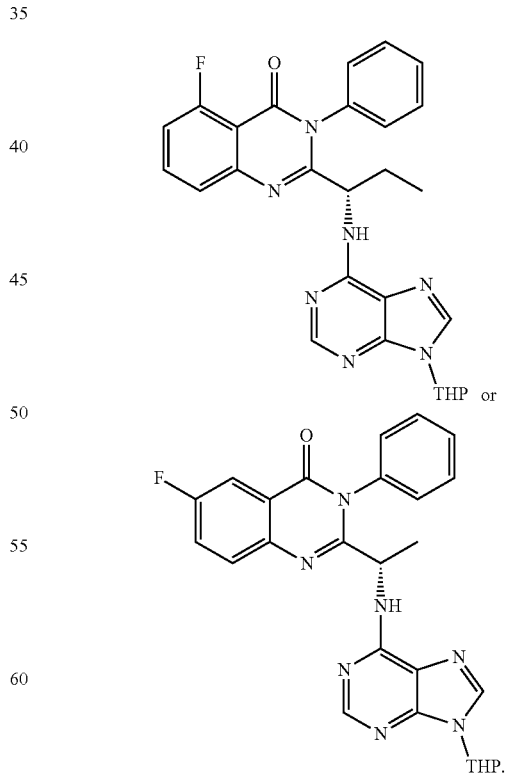

In some of the foregoing embodiments, the compound of formula I is

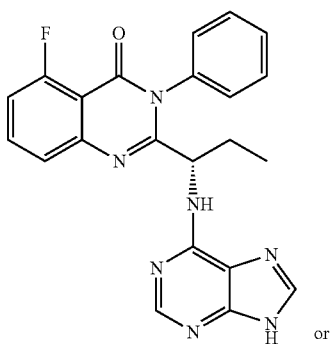

or a salt thereof.

In some of the foregoing embodiments, the compound of formula I is

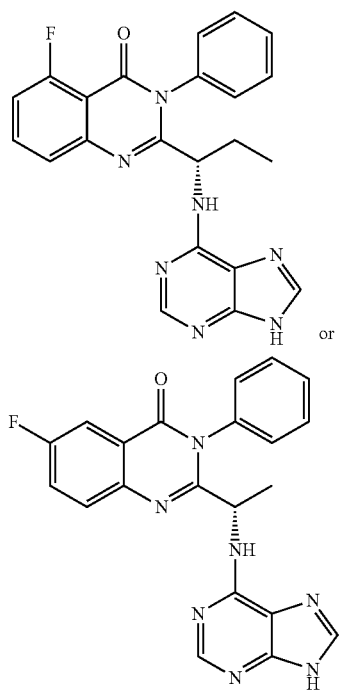

or a pharmaceutically acceptable salt thereof.

In some of the foregoing embodiments, the compound of formula I is

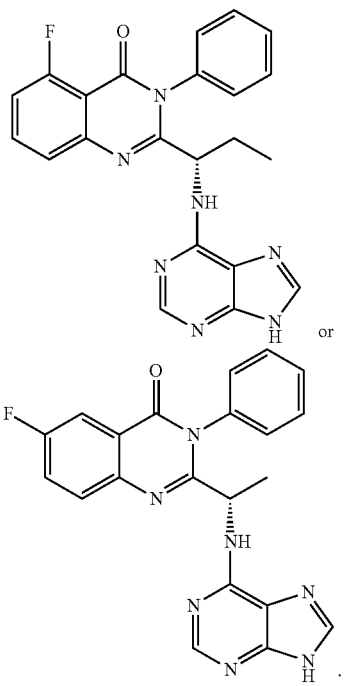

The processes described herein provide an efficient synthesis. In addition, the processes reduce or minimize certain process steps and/or side products, such as racemization of chiral centers during deprotection conditions. Furthermore, the processes disclosed herein may be suitable for various purposes, such as one or more of laboratory, industrial, commercial, non-commercial, manufacturing, non-manufacturing, regulatory, non-regulatory, medical, non-medical, pharmaceutical, and experimental uses.

By way of example, the processes of the present application may be suitable for making compounds of the formulas disclosed herein, in the amounts of ling, 5 mg, 10 mg, 50 mg, 100 mg, 250 mg, 500 mg, 750 mg, 1 g, 5 g, 1.0 g, 50 g, 100 g, 250 g, 500 g, 1 kg, 5 kg, 10 kg, 50 kg, 100 kg, 250 kg, 500 kg, 750 kg, 1000 kg, 2500 kg, and 5000 kg, in a single batch. In addition, the processes of the present application may be suitable for making compounds in the amounts between 1-100 mg, 1-500 mg, 1-1000 mg, 1-100 g, 1-500 g, 1-1000 g, 10-1000 kg, 500-1000 kg, 1000-2000 kg, 1000-5000 kg, and more than 5000 kg in a single batch. Additionally, the processes of the present application may be suitable for making compound in the amounts of at least 1 mg, 100 mg, 1 g, 10 g, 100 g, 11 g, 10 kg, 1.00 kg, 1000 kg, 2500 kg, and 5000 kg, in a single batch. Also, the processes described herein may be used for making compounds in single or multiple batches, or in continuous/semi-continuous processes. In some embodiments, the process is a batch process. In some embodiments, the process is a continuous process. In some other embodiments, the process is a semi-continuous process.

By way of example, the processes of the present application may utilize at least about 1 mmol, 10 mmol, 100 mmol, 1 mol, 5 mol, 10 mol, 20 mol, 50 mol, or 100 mol of at least one starting material. The starting material includes any of the starting or intermediate compounds disclosed herein, a salt thereof, or a reagent.

Compounds

In some embodiments, the application discloses the compound of formula 1:

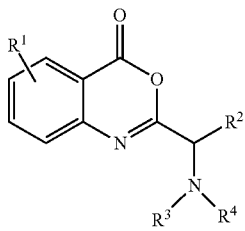

(1)

or a salt thereof, wherein $R^1$ is selected from the group consisting of halo and optionally substituted $C_1$-$C_8$ alkyl; $R^2$ is selected from the group consisting of H and optionally substituted $C_1$-$C_8$ alkyl, and $R^3$ and $R^4$ are each independently selected from the group consisting, of an amino protective group and an optionally substituted purinyl group. In some embodiments, $R^1$ is selected from the group consisting of halo and $C_1$-$C_8$ alkyl. In some embodiments, $R^1$ is halo. In some embodiments, $R^2$ is selected from the group consisting of H and $C_1$-$C_8$ alkyl. In some embodiments, $R^2$ is $C_1$-$C_8$ alkyl. In some embodiments, $R^2$ is $C_1$-$C_4$ alkyl. In some embodiments, $R^1$ is selected from the group consisting of halo and $C_1$-$C_8$ alkyl; $R^2$ is selected from the group consisting of H and $C_1$-$C_8$ alkyl, and $R^3$ and $R^4$ are each independently selected from the group consisting of an amino protective group and an optionally substituted purinyl group. In some embodiments, $R^1$ is halo; $R^2$ is $C_1$-$C_8$ alkyl, and $R^3$ and $R^4$ are each independently selected from the group consisting of an amino protective group and an optionally substituted purinyl group. In some embodiments, $R^1$ is halo; $R^2$ is $C_1$-$C_4$ alkyl, and $R^3$ and $R^4$ are each independently selected from the group consisting of an amino protective group and an optionally substituted purinyl group. In further embodiments, $R^3$ is an amino protective group and $R^4$ is an optionally substituted purinyl group. In further embodiments, $R^3$ and $R^4$ are amino protective groups. In further embodiments, $R^3$ is an amino protective group and $R^4$ is a purinyl group.

In some embodiments, the application discloses the compound of formula 1:

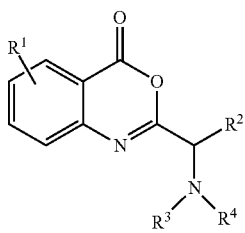

(1)

or a salt thereof; and wherein the compound of formula 1 or a salt thereof is synthesized by a process comprising step a) combining a compound of formula 2:

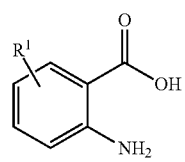

(2)

or a salt thereof, and a compound of formula 3:

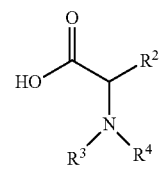

(3)

wherein the compound of formula 1 or a salt thereof is synthesized, wherein $R^1$ is halo;

$R^2$ is selected from the group consisting of H, and optionally substituted $C_1$-$C_8$ alkyl; and $R^3$ and $R^4$ are each independently selected from the group consisting of an amino protective group and an optionally substituted purinyl group. In other embodiments, $R^1$, $R^2$, $R^3$ and $R^4$ are as defined above for the compound of formula 1.

In some embodiments, the application discloses the compound of formula 8:

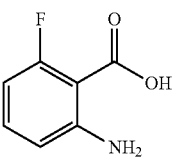

(8)

or a salt thereof, wherein the compound of formula 8 or a salt thereof is synthesized by the process comprising combining a compound of formula 9:

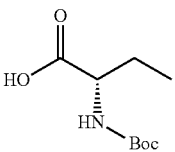

(9)

or a salt thereof, and a compound of formula 10:

(10)

wherein the compound of formula 8 or a salt thereof is synthesized.

In some embodiments, the application discloses a compound of formula 14:

(14)

[Structure of compound 14: 5-fluoro-3-phenyl-2-[(1S)-1-(9-THP-9H-purin-6-ylamino)propyl]quinazolin-4(3H)-one]

or a salt thereof, wherein the compound of formula 14 or a salt thereof is synthesized by a process comprising combining a compound of formula 12:

(12)

[Structure of compound 12: 2-[(1S)-1-aminopropyl]-5-fluoro-3-phenylquinazolin-4(3H)-one]

or a salt thereof, and
a compound of formula 13:

(13)

[Structure of compound 13: 6-chloro-9-THP-9H-purine]

wherein the compound of formula 14 is synthesized. In further embodiments, the process further comprises combining a compound of formula 11:

(11)

[Structure of compound 11: Boc-protected aminopropyl fluoroquinazolinone]

or a salt thereof, and
an acid, wherein the compound of formula 12 or a salt thereof is synthesized. In some embodiments, the process comprises combining a compound of formula 11:

(11)

[Structure of compound 11]

and an acid, wherein the compound of formula 12 or a salt thereof is synthesized. In yet further embodiments, the process further comprises combining a compound of formula 8:

(8)

[Structure of compound 8: benzoxazinone intermediate]

or a salt thereof, and aniline, wherein the compound of formula 11 is synthesized. In yet another embodiment, the process further comprises combining compound of formula 9:

(9)

[Structure of compound 9: 2-amino-6-fluorobenzoic acid]

or a salt thereof,
and a compound of formula 10:

(10)

[Structure of compound 10: N-Boc-L-2-aminobutyric acid]

wherein the compound of formula 8 or a salt thereof is synthesized.

In some embodiments, the application discloses a compound of formula 15:

(15)

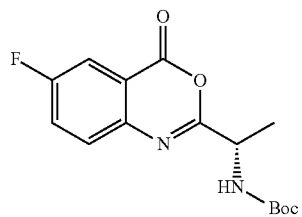

or a salt thereof, wherein the compound of formula 15 or a salt thereof is synthesized by a process comprising combining a compound of formula 16:

(16)

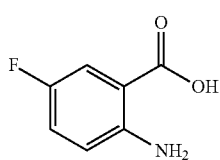

or a salt thereof,
and a compound of formula 10a:

(10a)

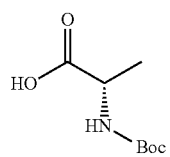

wherein the compound of formula 15 or a salt thereof is synthesized.

In some embodiments, the application discloses a compound of formula 15a:

(15a)

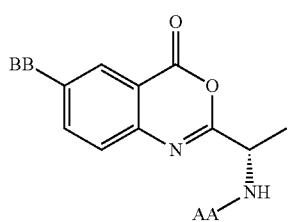

or a salt thereof, wherein the compound of formula 15a or a salt thereof is synthesized by a process comprising combining a compound of formula 16:

(16)

or a salt thereof, wherein BB is halo, and a compound of formula 10a:

(10b)

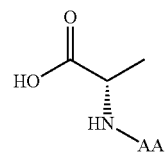

wherein AA is an amino protective group and wherein the compound of formula 15 or a salt thereof is synthesized. In some embodiments, BB is F. In some embodiments, the amino protective group is selected from the group consisting of t-butyl carbamate, tetrahydropyranyl, alkylsilyl, benzyl, an optionally substituted purinyl group, and alkoxymethyl. In other embodiments, the amino protective group is carbamate. In some embodiments, the amino protective group is t-butyl carbamate (BOC) or 9-fluoroenylmethyl carbamate (FMOC). In some embodiments, AA is t-butyl carbamate (BOC).

In some embodiments, the application discloses a compound of formula 19:

(19)

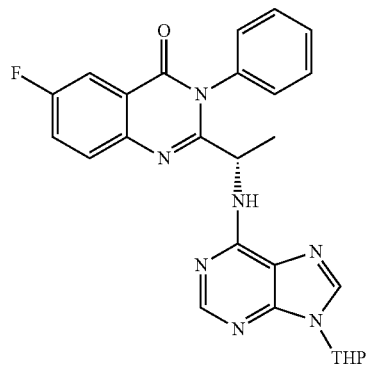

or a salt thereof, wherein the compound of formula 19 or a salt thereof is synthesized by a process comprising combining a compound of formula 18:

(18)

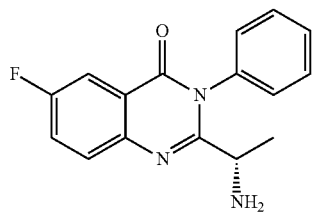

or a salt thereof, and a compound of formula 13:

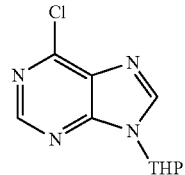
(13)

wherein a compound of formula 19 or a salt thereof is synthesized. In further embodiments, the process further comprises combining a compound of formula 17:

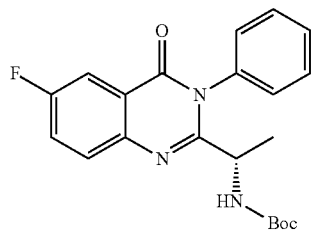
(17)

or a salt thereof, and an acid, wherein the compound of formula 18 or a salt thereof is synthesized. In some embodiments, the process further comprises combining a compound of formula 17:

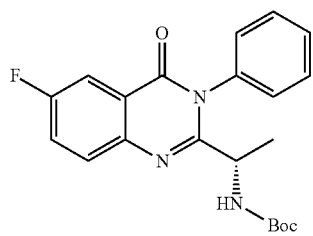
(17)

and an acid, wherein the compound of formula 18 or a salt thereof is synthesized. In yet further embodiments, the process further comprises combining a compound of formula 15:

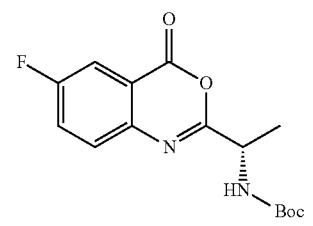
(15)

or a salt thereof, and aniline, wherein the compound of formula 17 is synthesized. In yet another embodiment, the process further comprises combining compound of formula 16:

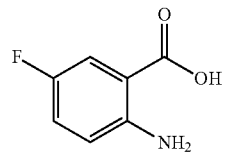
(16)

or a salt thereof,
and a compound of formula 10:

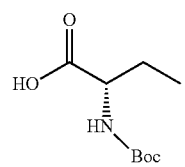
(10)

wherein the compound of formula 15 or a salt thereof is synthesized.

In some embodiments, the application discloses a compound of formula 20:

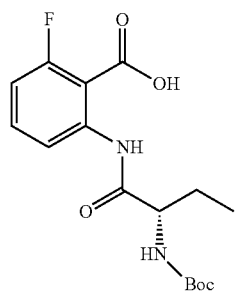
(20)

or a salt thereof, wherein the compound of formula 20 or a salt thereof is synthesized by a process comprising combining a compound of formula 9:

(9)

and
a compound of formula 10:

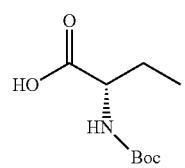
(10)

wherein the compound of formula 20 or a salt thereof is synthesized. In some embodiments, the process further comprises synthesizing a compound of formula 8:

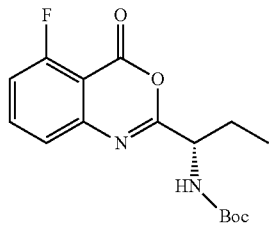
(8)

or a salt thereof. In some embodiments, the compound of formula 8 or a salt thereof ring-opens to form the compound of formula 20 or a salt thereof. In some embodiments, the compound of formula 20 is an intermediate that is formed during the preparation of the compound of formula 8.

A compound of formula 21:

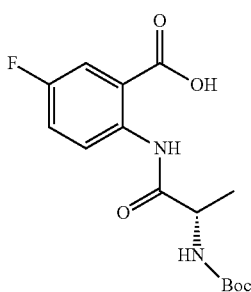
(21)

or a salt thereof, wherein the compound of formula 21 or a salt thereof is synthesized by a process comprising combining a compound of formula 16:

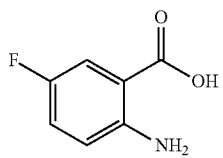
(16)

or a salt thereof, and a compound of formula 10a:

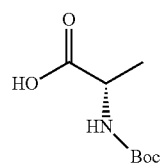
(10a)

wherein the compound of formula 21 or a salt thereof is synthesized. In some embodiments, the process further comprises synthesizing a compound of formula 15:

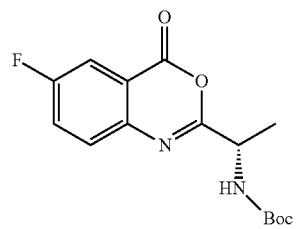
(15)

or a salt thereof. In some embodiments, the compound of formula 15 or a salt thereof ring-opens to form the compound of formula 21 or a salt thereof. In some embodiments, the compound of formula 21 is an intermediate that is formed during the preparation of the compound of formula 15.

By way of example, the compositions of the present application may comprise at least 2000 kg, 1000 kg, 750 kg, 500 kg, 250 kg, 100 kg, 10 kg, 1 kg, 0.5 kg, 50 g, 5 g, or 5 g of a compound of a formula disclosed herein or a salt thereof. In some embodiments, compositions may comprise a multi-kilogram amount of a compound of a formula disclosed herein or salt thereof. In other embodiments, compositions of the present disclosure may comprise at least about 1 mmol, 10 mmol, 100 mmol, 1 mol, 5 mol, 10 mol, 20 mol, 50 mol, or 100 mol of a compound of a formula disclosed herein or a salt thereof. In addition to a compound of a formula disclosed herein or a salt thereof, composition may further comprise solvents, reagents, or combinations thereof. In another aspect, compositions may consist essentially of a compound of a formula disclosed herein or a salt thereof.

By way of example, the resulting compounds from the processes described herein may be used in a pharmaceutical composition. In another embodiment, provided is a pharmaceutical composition comprising a resulting compound from the processes disclosed herein or a salt thereof, and one or more pharmaceutically acceptable carriers or excipients.

EXAMPLES

Example 1. Synthesis of a Compound of Formula 17

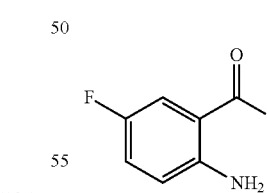
16
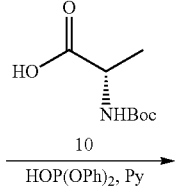
10
HOP(OPh)$_2$, Py

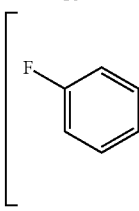
15
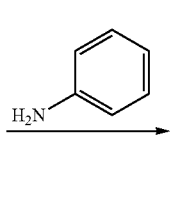

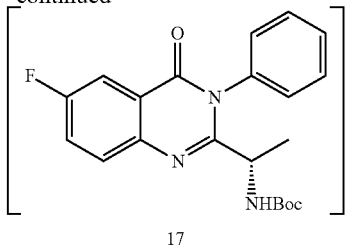

17

A compound of formula 16 (1.0 kg, 1.0 eq), a compound of formula 10 (1.5 kg, 1.2 eq) and pyridine (3.0 kg) were added to reactor A. The mixture was agitated at 19 to 25° C. and diphenylphosphite (6.1 kg, 4.0 eq) was added to the mixture over at least 2 h while maintaining the internal temperature at less than about 35° C. The reaction mixture was adjusted to 19 to 25° C. and agitated until the reaction was deemed complete by HPLC analysis (1-3 h). Aniline (0.7 kg, 1.2 eq) was added over a minimum of 1 h while maintaining the internal temperature at less than about 40° C. The reaction mixture was then adjusted to 45 to 55° C. and agitated until the reaction is deemed complete. The reaction mixture was cooled to 19 to 25° C. and toluene (13 kg) was added followed by a prepared 1M HCl solution (10 kg) while maintaining the internal temperature, at less than about 30° C. The biphasic mixture was agitated at about 22° C. for at least 30 minutes and then allowed to settle. The aqueous layer was separated and discarded. A second portion of 1M HCl (10 kg) was added to the organic layer in reactor A. The biphasic mixture was agitated at 19 to 25° C. for at least 30 minutes and then allowed to settle. The aqueous layer was separated and discarded. A compound of formula 17 was carried forward to the next step as a stock solution in toluene.

Example 2. Synthesis of a Compound of Formula 18

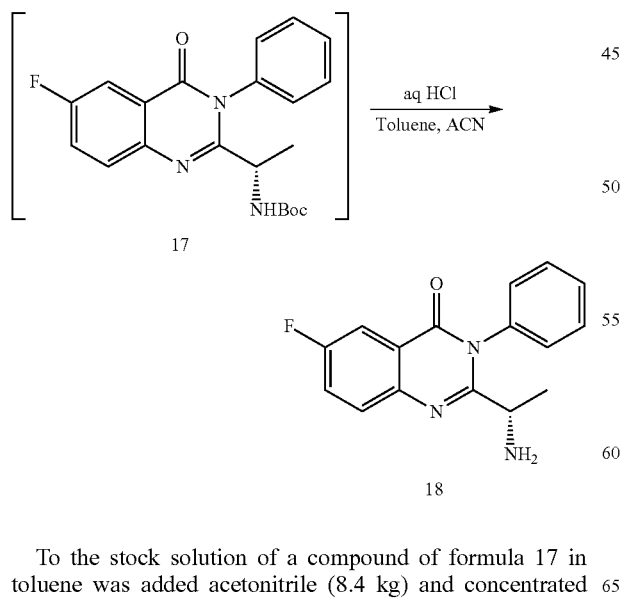

To the stock solution of a compound of formula 17 in toluene was added acetonitrile (8.4 kg) and concentrated HCl (2.2 kg) while maintaining the internal temperature at no more than 30° C.

The reaction mixture was adjusted to 19 to 25° C. and agitated until the reaction was deemed complete. Water (5 kg) was added and the biphasic mixture was agitated at 19 to 25° C. for at least 30 minutes and then allowed to settle. The bottom aqueous layer was separated and transferred to reactor B (product was in the aqueous layer). Water (10 kg) was then added to the organic layer in reactor A. The biphasic mixture was agitated at 19 to 25° C. for at least 30 minutes and then allowed to settle. The bottom aqueous layer was separated and transferred to reactor B (combining with the first aqueous phase). Toluene (4 kg) was added to the combined aqueous layers in reactor B and the biphasic mixture was agitated at 19 to 25° C. for at least 30 minutes and then allowed to settle. The bottom aqueous layer was separated and transferred to reactor A. Toluene (4 kg) was added to reactor A and the biphasic mixture was agitated at 19 to 25° C. for at least 30 minutes and then allowed to settle. The bottom aqueous layer was separated and transferred to reactor B. The aqueous phase was then partially concentrated under vacuum to 18 to remove toluene and reduce acetonitrile levels to no more than 3.5%. The aqueous phase was then transferred, in portions, to reactor B containing water (5 kg), ammonium hydroxide (6.5 kg, 8.0 eq) and acetonitrile (0.8 kg) while maintaining the internal temperature at no more than 19 to 25° C. The resulting slurry was agitated at 19 to 25° C. for ca 1 h before filtering. The filter cake was rinsed with water (3 kg) and then dried under vacuum at no more than 50° C. to afford 18. $^1$H NMR (400 MHz, CDCl$_3$): δ 7.82 (dd, J=8.4, 2.2 Hz, 1H), 7.71 (dd, J=9.2, 5.0 Hz, 1H), 7.55-7.45 (m, 4H), 7.27 (d, J=6.4 Hz, 2H), 3.69 (q, 6.4 Hz, 1H), 2.01 (s, 2H), 1.27 (d, J=6.0 Hz, 3H). $^{13}$C NMR (100 MHz, CDCl$_3$): δ 162.3, 161.9, 160.5, 159.8, 144.4, 136.6, 130.3, 130.2, 129.9, 129.0, 128.9, 128.4, 123.4, 123.2, 1.22.3, 122.2, 112.1, 111.9, 48.7, 23.7 (signal splitting due to fluorine results in additional peaks).

Example 3. Synthesis of a Compound of Formula 19

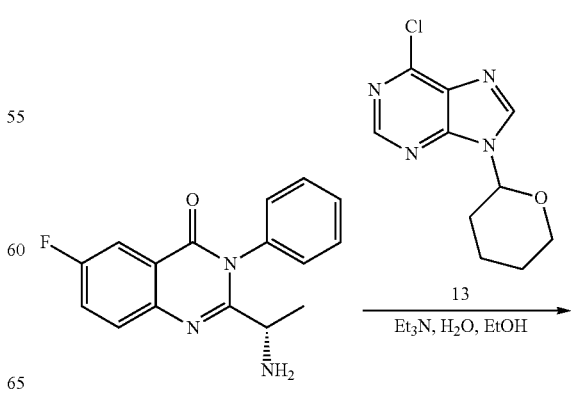

-continued

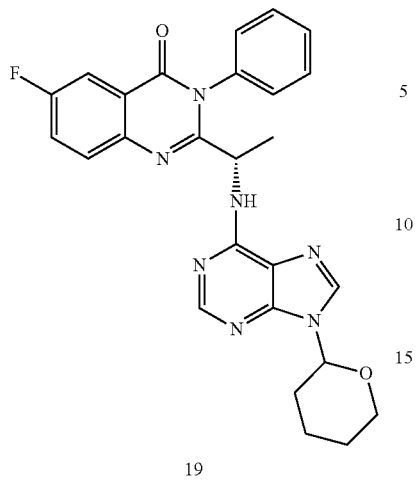

19

A compound of formula 18 (1.0 kg, a compound of formula 13 (0.9 kg, 1.1 eq), triethylamine (0.5 kg, 1.5 eq), water (4 kg) and EtOH (2 kg) were added to reactor A. The mixture was adjusted to 75 to 85° C. and agitated until the reaction was deemed complete. The mixture was then adjusted to 19 to 25° C. and agitated for ca 1 h before filtering. The isolated compound of formula 19 solid was rinsed with water (2 kg) and heptanes (2×3 kg) and then dried under vacuum. $^1$H NMR (400 MHz, CDCl$_3$): δ 8.28 (d, J=2 Hz, 1H), 8.00 (bs, 1H), 7.89 (dd, J=8.8, 3.0 Hz, 1H), 7.73 (m, 1H), 7.59 (m, 3H), 7.48 (m, 2H), 7.35 (m, 1H), 6.68 (m, 1H), 5.69 (dd, J=10.0, 3.0 Hz, 1H), 5.24 (bs, 1H), 4.1.6 (dd, J=11.6, 2.0 Hz, 1H), 3.77 (tt, J=11.2, 1.4 Hz, 1H), 2.06 (m, 3H), 1.75 (m, 3H), 1.47 (d, J=6.8 Hz, 3H).

Example 4. Synthesis of a Compound of Formula III

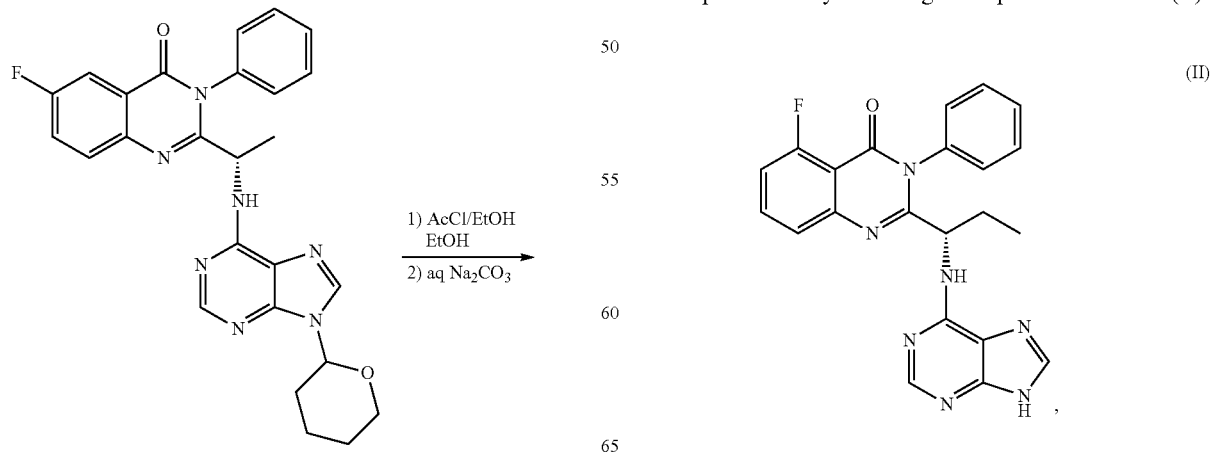

-continued

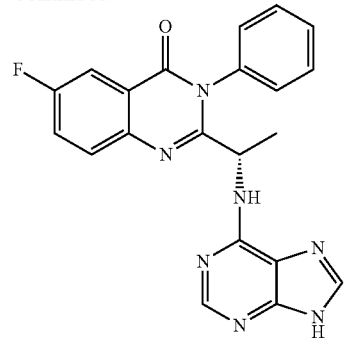

III

To reactor A was added a compound of formula 19 followed by EtOH (4.2 kg). Acetyl chloride (0.33 kg, 1.2 eq) was then added slowly while maintaining the internal temperature at less than about 40° C. The mixture was then adjusted to 19 to 25° C. and agitated until the reaction was deemed complete. After adjusting the temperature to 5 to 15° C., 0.84 kg of a prepared 4.5% sodium carbonate solution was added to the reaction mixture followed by water (1 kg) while maintaining the internal temperature at 5 to 15° C. To reactor B was added 5.44 kg of a prepared 4.5% sodium carbonate solution and the contents were warmed to 65 to 75° C. Approximately 20% of the solution held in reactor A was then transferred to the aqueous solution in reactor B while keeping the internal temperature at 65 to 75° C. The mixture was aged for about 30 minutes until a slurry was formed. The remaining solution from reactor. A was transferred to reactor B over a period of about 1 h while maintaining the internal temperature at 65 to 75° C. The slurry was agitated at 65 to 75° C. for 1 to 5 h until a thick slurry was formed. The contents were then adjusted to 1.9 to 25° C. over about 1 h and agitated about 1 h before filtering. The wet cake was rinsed with water (10 kg) and then dried under vacuum at about 65° C. $^1$H NMR (400 MHz, CDCl$_3$): δ 8.33 (s, 1H), 7.98 (br, 1H), 7.90 (dd, J=8.4, 2.8 Hz, 1H), 7.74 (dd, J=8.8, 5.2 Hz, 1H), 7.65-7.57 (m, 3H), 7.51-7.45 (m, 2H), 7.37 (m, 1H), 6.84 (bd, J=8.8 Hz, 1H), 5.27 (br, 1H), 1.75 (br, 1H), 1.50 (d, J=6.8 Hz, 3H). $^{19}$F NMR (400 MHz, CDCl$_3$): δ −111.11 (referenced to TFA at −76.5 ppm).

The invention claimed is:
1. A process for synthesizing a compound of formula (II):

or a salt thereof, comprising combining a compound of formula (14):

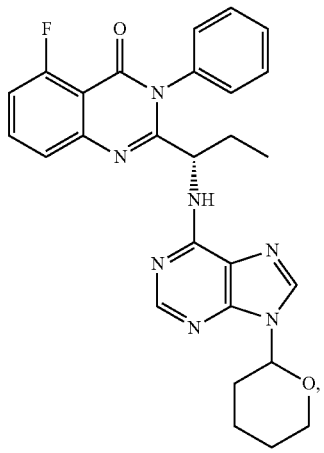

(14)

or a salt thereof, and one or more reagents to remove the amino protective group tetrahydropyranyl (THP) from the compound of formula (14), wherein the one or more reagents comprise an acid, and wherein the compound of formula (14), or a salt thereof, and the one or more reagents are combined under conditions having less than 0.5% water present.

2. The process of claim 1, further comprising combining a compound of formula (12):

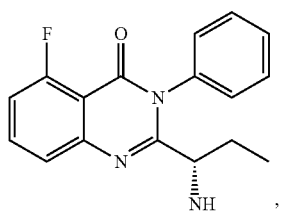

(12)

or a salt thereof, and a compound of formula (13):

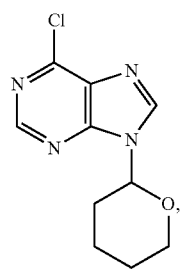

(13)

to provide the compound of formula (14), or a salt thereof.

3. The process of claim 2, further comprising combining a compound of formula (11):

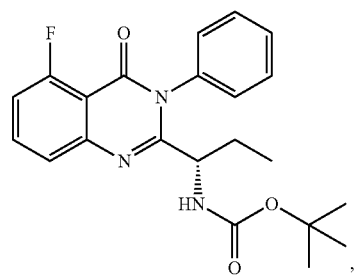

(11)

or a salt thereof, and one or more reagents to remove the amino protective group t-butyl carbamate (BOC) from the compound of formula (11), or a salt thereof, to provide the compound of formula (12), or a salt thereof, wherein the one or more reagents comprise an acid.

4. The process of claim 2, wherein the compound of formula (14), or a salt thereof, is crystallized from one or more solvents selected from the group consisting of alcohol, water, and combinations thereof.

5. The process of claim 3, wherein the one or more reagents combined with the compound of formula (11), or a salt thereof, comprises a mineral acid or trifluoroacetic acid (TFA).

6. The process of claim 5, wherein the mineral acid is hydrochloric acid.

7. The process of claim 3, comprising combining the compound of formula (11), or a salt thereof, and the one or more reagents in the presence of a solvent selected from the group consisting of acetonitrile, methanol, ethanol, isopropanol, n-propanol, tetrahydrofuran (THF), water, toluene and mixtures thereof.

8. The process of claim 3, comprising combining the compound of formula (11), or a salt thereof, and the one or more reagents at a temperature between 0 and 70 degrees Celsius.

9. The process of any one of claim 3, wherein the compound of formula (12), or a salt thereof, is crystallized from one or more solvents selected from the group comprising water, methanol, ethanol, isopropanol, n-propanol, concentrated NH$_4$OH, acetonitrile, MTBE, DCM, EtOAc, iPrOAc, toluene, 2-Me-THF, DIPE (diisopropylether), heptane and heptanes.

10. The process of claim 9, wherein the one or more solvents are i) water, concentrated NH$_4$OH, and acetonitrile; or ii) isopropanol and toluene.

11. The process of claim 2, further comprising combining the compound of formula (12), or a salt thereof, and the compound of formula (13) with a base selected from the group consisting of triethylamine, pyridine, Hunig's base, and a carbonate base.

12. The process of claim 11, wherein the base is triethylamine.

13. The process of claim 2, wherein the compound of formula (12), or a salt thereof, and the compound of formula (13) are combined in the presence of a solvent selected from the group consisting of water, an alcoholic solvent, and combinations thereof.

14. The process of claim 2, wherein the compound of formula (12), or a salt thereof, and the compound of formula (13) are combined at a temperature between 35 and 110 degrees Celsius.

15. The process of claim 1, wherein the one or more reagents combined with the compound of formula (14), or a salt thereof, are selected from the group consisting of a mineral acid, TFA and a Lewis acid.

16. The process of claim 15, wherein mineral acid is hydrochloric acid.

17. The process of claim 1, wherein the compound of formula (14), or a salt thereof, and the one or more reagents are combined under non-aqueous acidic reaction conditions.

18. The process of claim 1, wherein the compound of formula (14), or a salt thereof, and the one or more reagents are combined under anhydrous conditions.

19. The process of claim 1, wherein the process is performed at a temperature between 30 and 70 degrees Celsius.

20. The process of claim 1, wherein the compound of formula (II), or a salt thereof, is crystallized from one or more solvents selected from the group comprising water, ethanol, methanol, isopropanol, n-propanol, and acetone.

21. The process of claim 20, wherein the one or more solvents are i) water and ethanol; or ii) acetone.

22. The process of claim 2, wherein the compound of formula (14), or a salt thereof, is crystallized from one or more solvents selected from the group consisting of isopropanol, n-propanol, ethanol, methanol, and water.

23. The process of claim 1, wherein the process is operated in a batch process.

24. The process of claim 1, wherein at least 90% of the compound of formula (14), or a salt thereof, is deprotected to provide the compound of formula (II), or a salt thereof.

* * * * *